United States Patent
Nielsen et al.

(10) Patent No.: US 8,119,387 B2
(45) Date of Patent: Feb. 21, 2012

(54) **POLYPEPTIDES OF STRAIN *BACILLUS* SP. P203**

(75) Inventors: Preben Nielsen, Horsholm (DK); Reinhard Wilting, Farum (DK); Martin Borchert, Alleroed (DK)

(73) Assignee: Novozymes A/S, Bagsvaerd (DK)

( * ) Notice: Subject to any disclaimer, the term of this patent is extended or adjusted under 35 U.S.C. 154(b) by 653 days.

(21) Appl. No.: 12/063,599

(22) PCT Filed: Aug. 15, 2006

(86) PCT No.: PCT/DK2006/000447
§ 371 (c)(1),
(2), (4) Date: Feb. 12, 2008

(87) PCT Pub. No.: WO2007/019859
PCT Pub. Date: Feb. 22, 2007

(65) Prior Publication Data
US 2010/0151111 A1   Jun. 17, 2010

Related U.S. Application Data

(60) Provisional application No. 60/709,264, filed on Aug. 18, 2005.

(30) Foreign Application Priority Data

Aug. 16, 2005  (DK) ................. 2005 01156

(51) Int. Cl.
    *C12N 9/88*   (2006.01)
(52) U.S. Cl. .................. 435/232; 424/94.65
(58) Field of Classification Search .......... None
    See application file for complete search history.

(56) References Cited

U.S. PATENT DOCUMENTS

2006/0259995 A1   11/2006   Cayouette et al.

FOREIGN PATENT DOCUMENTS

| JP | 2004154006 | 6/2004 |
| WO | WO 01/77315 | 10/2001 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Takami et al., Swiss-Prot Accession Q9KFW1, Oct. 1, 2000.*
Tripp et al., The Journal of Biological Chemistry, vol. 276, No. 52, pp. 48615-18618 (2001).
Marchler-Bauer et al., Nucleic Acids Research, vol. 33, pp. D192-D196 (2005).
Koki Horikoshi, Microbiology and Molecular Biology Reviews, vol. 63, No. 4, pp. 735-750 (1999).
Takami et al., Nucleic Acids Research, vol. 28, No. 21, pp. 4317-4331 (2000).
Database EMBL, Accession No. Q5WD44, XP-002488947 (2004).
Fleischmann et al, Whole Genome Sequences and Assembly of Haemophilus Influenzae Rd; Nature, vol. 269, pp. 496-512 (1995).
Van Dijl et al, Protein Transport pathways in *Bacillus subtilis*: a genome-based road map; in *Bacillus subtilis* and its closest relatives-From genes to cells; p. 337-355; A.L. Sonenshein (ed.); ASM Press (2002).
Power et al., "Secretion and autoproteolytic maturation of subtilisin", Proc Nat Acad Sci USA 83(10), 3096-3100 (1986).
UniProt, Access No. Q5WK14 (2004).

* cited by examiner

*Primary Examiner* — Richard Hutson
(74) *Attorney, Agent, or Firm* — Michael W. Krenicky

(57) ABSTRACT

A new strain *Bacillus* sp. P203 (*Bacillus plakortiensis*) is disclosed. Isolated mature functional polypeptide which is obtainable from the bacterium strain *Bacillus* sp. P203 deposited under accession number DSM 17419 are disclosed.

13 Claims, 2 Drawing Sheets

SEQUENCE LISTING

```
<160> NUMBER OF SEQ ID NOS: 21

<210> SEQ ID NO 1
<211> LENGTH: 1953
<212> TYPE: DNA
<213> ORGANISM: Bacillus sp. P 203
<220> FEATURE:
<221> NAME/KEY: CDS
<222> LOCATION: (1)..(1953)
<223> OTHER INFORMATION: serine protease
<220> FEATURE:
<221> NAME/KEY: sig_peptide
<222> LOCATION: (1)..(111)
<220> FEATURE:
<221> NAME/KEY: mat_peptide
<222> LOCATION: (112)..(1953)

<400> SEQUENCE: 1 atg aat aaa caa aat aca caa tat ttt gag agg agc gct gcg atg aat      48
Met Asn Lys Gln Asn Thr Gln Tyr Phe Glu Arg Ser Ala Ala Met Asn
        -35                 -30                 -25 atc gat aaa aag aaa caa aaa ccg tgg aac gta atg gta tta acc gca      96
Ile Asp Lys Lys Lys Gln Lys Pro Trp Asn Val Met Val Leu Thr Ala
    -20                 -15                 -10 ctg tca aca agt ttg gta ttc gga ggg ttt ggc tat tct cca caa caa     144
Leu Ser Thr Ser Leu Val Phe Gly Gly Phe Gly Tyr Ser Pro Gln Gln
-5                  -1  1               5                  10 gta tca gct gaa aca aaa act ggt tca ctc aat cta tca gat gac atc     192
Val Ser Ala Glu Thr Lys Thr Gly Ser Leu Asn Leu Ser Asp Asp Ile
                15                  20                  25 aaa tta gat agt act gag acg gtc tct gtc atc gtt gag cta gaa gaa     240
Lys Leu Asp Ser Thr Glu Thr Val Ser Val Ile Val Glu Leu Glu Glu
            30                  35                  40 tct ccc gag cat tta gcg att gca gaa gca ctt gaa aaa ggt gag gat     288
Ser Pro Glu His Leu Ala Ile Ala Glu Ala Leu Glu Lys Gly Glu Asp
        45                  50                  55 cta aca gaa tcg caa gca aaa gca aag gta gaa gcg tct cag gat tca     336
Leu Thr Glu Ser Gln Ala Lys Ala Lys Val Glu Ala Ser Gln Asp Ser
60                  65                  70                  75
```

```
ttt gag gaa gac tta tct act aaa caa tca tct tat aca att aca cat    384
Phe Glu Glu Asp Leu Ser Thr Lys Gln Ser Ser Tyr Thr Ile Thr His
             80                  85                  90 acg tat caa tcc gtt ttt aat ggt ttt acc att gaa tta cct gca aat    432
Thr Tyr Gln Ser Val Phe Asn Gly Phe Thr Ile Glu Leu Pro Ala Asn
             95                 100                 105 caa tta gaa gca ctt tca gag att gac ggt gtt aaa acc gtc tgg gaa    480
Gln Leu Glu Ala Leu Ser Glu Ile Asp Gly Val Lys Thr Val Trp Glu
        110                 115                 120 aac gaa gag gtt caa ctc att gat cct gta tta gaa gaa agt gtt cta    528
Asn Glu Glu Val Gln Leu Ile Asp Pro Val Leu Glu Glu Ser Val Leu
        125                 130                 135 gaa gaa gcg att gaa ccc tat atg gca gat agt gtg cct tat cta ggt    576
Glu Glu Ala Ile Glu Pro Tyr Met Ala Asp Ser Val Pro Tyr Leu Gly
140                 145                 150                 155 gtt gat cga ctc cat att gat ggg atc act ggt gaa ggg gta aaa gtc    624
Val Asp Arg Leu His Ile Asp Gly Ile Thr Gly Glu Gly Val Lys Val
                160                 165                 170 gga gtc att gat act ggt gtt gat tac aca cac cct gac ctt aca gca    672
Gly Val Ile Asp Thr Gly Val Asp Tyr Thr His Pro Asp Leu Thr Ala
            175                 180                 185 gcc tac aaa ggt gga tat gac ttt gtc gat aat gat gat gca caa        720
Ala Tyr Lys Gly Gly Tyr Asp Phe Val Asp Asn Asp Asp Ala Gln
            190                 195                 200 gaa aca acc tac gat gat tgg tta gca tca gga atg ccg gaa ttt aat    768
Glu Thr Thr Tyr Asp Asp Trp Leu Ala Ser Gly Met Pro Glu Phe Asn
        205                 210                 215 atc aat gga agt tcg tat tat aca tca cat ggt aca cat gtt gct ggc    816
Ile Asn Gly Ser Ser Tyr Tyr Thr Ser His Gly Thr His Val Ala Gly
220                 225                 230                 235 acc att gct gga caa ggt gat aac gaa tct gat ttt gcc aca aca ggt    864
Thr Ile Ala Gly Gln Gly Asp Asn Glu Ser Asp Phe Ala Thr Thr Gly
                240                 245                 250 att gca cct gac gct gac att tat tcc tat cga gta tta ggt cct tat    912
Ile Ala Pro Asp Ala Asp Ile Tyr Ser Tyr Arg Val Leu Gly Pro Tyr
            255                 260                 265 gga tca ggt aca aca gca aat gta ctt ggt ggt att gaa ctt tct gtt    960
Gly Ser Gly Thr Thr Ala Asn Val Leu Gly Gly Ile Glu Leu Ser Val
        270                 275                 280 gaa gat gga atg gat gtt att aat cta tct ctt ggg gct aat gtt aac    1008
Glu Asp Gly Met Asp Val Ile Asn Leu Ser Leu Gly Ala Asn Val Asn
        285                 290                 295 gat cca cta tac cct act agt gtt gca gta aat aat gct gtt tta gct    1056
Asp Pro Leu Tyr Pro Thr Ser Val Ala Val Asn Asn Ala Val Leu Ala
300                 305                 310                 315 ggc gtt acg gct gtt gtt tca gca ggt aac agt ggt aga gat ggt ctt    1104
Gly Val Thr Ala Val Val Ser Ala Gly Asn Ser Gly Arg Asp Gly Leu
                320                 325                 330 tat aca ctt ggt tca cca ggt acc tct cca ctt gcc att acg gtt ggt    1152
Tyr Thr Leu Gly Ser Pro Gly Thr Ser Pro Leu Ala Ile Thr Val Gly
            335                 340                 345 gcc aac gat gtg ccg tta gtg ttc act gac ttt act ggc tat ctt gat    1200
Ala Asn Asp Val Pro Leu Val Phe Thr Asp Phe Thr Gly Tyr Leu Asp
        350                 355                 360 gaa tca ttc tca gct ggc ctt gtg aat atc tca agc ggg ttt gat act    1248
Glu Ser Phe Ser Ala Gly Leu Val Asn Ile Ser Ser Gly Phe Asp Thr
        365                 370                 375 gat ttt gat gaa tta gaa gcg ggt gaa tat ggc att gtt tat gcc ggc    1296
Asp Phe Asp Glu Leu Glu Ala Gly Glu Tyr Gly Ile Val Tyr Ala Gly
380                 385                 390                 395
```

| | | | | | | | | | | | | | | | |
|---|---|---|---|---|---|---|---|---|---|---|---|---|---|---|---|
| ctt | ggt | tca | gtt | gca | gag | ttt | aat | cag | gtt | gat | gca | gaa | gga | aaa | gtt |
| Leu | Gly | Ser | Val | Ala | Glu | Phe | Asn | Gln | Val | Asp | Ala | Glu | Gly | Lys | Val |
| | | | 400 | | | | | 405 | | | | | 410 | | |

1344 gct ctt gtt gct cgt gga gaa ttg gcg ttt gta gat aaa att gca aat    1392
Ala Leu Val Ala Arg Gly Glu Leu Ala Phe Val Asp Lys Ile Ala Asn
        415                 420                 425 gct aaa gcc gct ggt gca gaa gcg att att atc tat aac aac ata ccg    1440
Ala Lys Ala Ala Gly Ala Glu Ala Ile Ile Ile Tyr Asn Asn Ile Pro
        430                 435                 440 gga gct gga cac atc cct aac tac ttt gga gaa ggc gtg aat ttt gtc    1488
Gly Ala Gly His Ile Pro Asn Tyr Phe Gly Glu Gly Val Asn Phe Val
        445                 450                 455 gct ggt ttc tct tta acc tat gag gat ggt att gct cta aga gat gcg    1536
Ala Gly Phe Ser Leu Thr Tyr Glu Asp Gly Ile Ala Leu Arg Asp Ala
460                 465                 470                 475 att acc gat gaa agc tca ttc tcg ttt ggt gac cga agc gaa tca caa    1584
Ile Thr Asp Glu Ser Ser Phe Ser Phe Gly Asp Arg Ser Glu Ser Gln
                480                 485                 490 act cca ggt ggt gta cta gct gat ttc agt tct cgt ggt cca gtt aat    1632
Thr Pro Gly Gly Val Leu Ala Asp Phe Ser Ser Arg Gly Pro Val Asn
                495                 500                 505 gaa tca ttt gca att aaa cct gaa gta agt gca cca ggt gtc aat acg    1680
Glu Ser Phe Ala Ile Lys Pro Glu Val Ser Ala Pro Gly Val Asn Thr
        510                 515                 520 tta tca cct gtt cct act tat atg aac ggt cct gac tat att ggc gat    1728
Leu Ser Pro Val Pro Thr Tyr Met Asn Gly Pro Asp Tyr Ile Gly Asp
        525                 530                 535 tac gag tac gcg tat ggg cgt aaa tca ggt aca tca atg tca gca cca    1776
Tyr Glu Tyr Ala Tyr Gly Arg Lys Ser Gly Thr Ser Met Ser Ala Pro
540                 545                 550                 555 cat gtt gca ggt aca gcg gcc ctt ctt ctt gaa gtg aag ccg gac tta    1824
His Val Ala Gly Thr Ala Ala Leu Leu Leu Glu Val Lys Pro Asp Leu
                560                 565                 570 tcg cca gca gac att aaa aca acg tta atg aat acg gct aat cca atg    1872
Ser Pro Ala Asp Ile Lys Thr Thr Leu Met Asn Thr Ala Asn Pro Met
                575                 580                 585 aca cta gat tat agt gtg ttt gaa att ggt gct ggg caa att gat caa    1920
Thr Leu Asp Tyr Ser Val Phe Glu Ile Gly Ala Gly Gln Ile Asp Gln
        590                 595                 600 cgg ctc tta ctc tta agt ttt gat cac gta agc                        1953
Arg Leu Leu Leu Leu Ser Phe Asp His Val Ser
        605                 610

<210> SEQ ID NO 2
<211> LENGTH: 651
<212> TYPE: PRT
<213> ORGANISM: Bacillus sp. P 203

<400> SEQUENCE: 2

Met Asn Lys Gln Asn Thr Gln Tyr Phe Glu Arg Ser Ala Ala Met Asn
        -35                 -30                 -25

Ile Asp Lys Lys Lys Gln Lys Pro Trp Asn Val Met Val Leu Thr Ala
        -20                 -15                 -10

Leu Ser Thr Ser Leu Val Phe Gly Gly Phe Gly Tyr Ser Pro Gln Gln
-5                  -1   1               5                   10

Val Ser Ala Glu Thr Lys Thr Gly Ser Leu Asn Leu Ser Asp Asp Ile
            15                  20                  25

Lys Leu Asp Ser Thr Glu Thr Val Ser Val Ile Val Glu Leu Glu Glu
        30                  35                  40

Ser Pro Glu His Leu Ala Ile Ala Glu Ala Leu Glu Lys Gly Glu Asp

```
                45                  50                  55
Leu Thr Glu Ser Gln Ala Lys Ala Lys Val Glu Ala Ser Gln Asp Ser
 60                  65                  70                  75

Phe Glu Glu Asp Leu Ser Thr Lys Gln Ser Ser Tyr Thr Ile Thr His
                     80                  85                  90

Thr Tyr Gln Ser Val Phe Asn Gly Phe Thr Ile Glu Leu Pro Ala Asn
                 95                 100                 105

Gln Leu Glu Ala Leu Ser Glu Ile Asp Gly Val Lys Thr Val Trp Glu
                110                 115                 120

Asn Glu Glu Val Gln Leu Ile Asp Pro Val Leu Glu Glu Ser Val Leu
            125                 130                 135

Glu Glu Ala Ile Glu Pro Tyr Met Ala Asp Ser Val Pro Tyr Leu Gly
140                 145                 150                 155

Val Asp Arg Leu His Ile Asp Gly Ile Thr Gly Glu Gly Val Lys Val
                160                 165                 170

Gly Val Ile Asp Thr Gly Val Asp Tyr Thr His Pro Asp Leu Thr Ala
                175                 180                 185

Ala Tyr Lys Gly Gly Tyr Asp Phe Val Asp Asn Asp Asp Asp Ala Gln
                190                 195                 200

Glu Thr Thr Tyr Asp Asp Trp Leu Ala Ser Gly Met Pro Glu Phe Asn
205                 210                 215

Ile Asn Gly Ser Ser Tyr Tyr Thr Ser His Gly Thr His Val Ala Gly
220                 225                 230                 235

Thr Ile Ala Gly Gln Gly Asp Asn Glu Ser Asp Phe Ala Thr Thr Gly
                240                 245                 250

Ile Ala Pro Asp Ala Asp Ile Tyr Ser Tyr Arg Val Leu Gly Pro Tyr
                255                 260                 265

Gly Ser Gly Thr Thr Ala Asn Val Leu Gly Ile Glu Leu Ser Val
                270                 275                 280

Glu Asp Gly Met Asp Val Ile Asn Leu Ser Leu Gly Ala Asn Val Asn
            285                 290                 295

Asp Pro Leu Tyr Pro Thr Ser Val Ala Val Asn Asn Ala Val Leu Ala
300                 305                 310                 315

Gly Val Thr Ala Val Val Ser Ala Gly Asn Ser Gly Arg Asp Gly Leu
                320                 325                 330

Tyr Thr Leu Gly Ser Pro Gly Thr Ser Pro Leu Ala Ile Thr Val Gly
                335                 340                 345

Ala Asn Asp Val Pro Leu Val Phe Thr Asp Phe Thr Gly Tyr Leu Asp
                350                 355                 360

Glu Ser Phe Ser Ala Gly Leu Val Asn Ile Ser Ser Gly Phe Asp Thr
365                 370                 375

Asp Phe Asp Glu Leu Glu Ala Gly Glu Tyr Gly Ile Val Tyr Ala Gly
380                 385                 390                 395

Leu Gly Ser Val Ala Glu Phe Asn Gln Val Asp Ala Glu Gly Lys Val
                400                 405                 410

Ala Leu Val Ala Arg Gly Glu Leu Ala Phe Val Asp Lys Ile Ala Asn
                415                 420                 425

Ala Lys Ala Ala Gly Ala Glu Ala Ile Ile Ile Tyr Asn Asn Ile Pro
                430                 435                 440

Gly Ala Gly His Ile Pro Asn Tyr Phe Gly Glu Gly Val Asn Phe Val
                445                 450                 455

Ala Gly Phe Ser Leu Thr Tyr Glu Asp Gly Ile Ala Leu Arg Asp Ala
460                 465                 470                 475
```

```
Ile Thr Asp Glu Ser Ser Phe Ser Phe Gly Asp Arg Ser Glu Ser Gln
                480                 485                 490

Thr Pro Gly Gly Val Leu Ala Asp Phe Ser Ser Arg Gly Pro Val Asn
            495                 500                 505

Glu Ser Phe Ala Ile Lys Pro Glu Val Ser Ala Pro Gly Val Asn Thr
        510                 515                 520

Leu Ser Pro Val Pro Thr Tyr Met Asn Gly Pro Asp Tyr Ile Gly Asp
    525                 530                 535

Tyr Glu Tyr Ala Tyr Gly Arg Lys Ser Gly Thr Ser Met Ser Ala Pro
540                 545                 550                 555

His Val Ala Gly Thr Ala Ala Leu Leu Leu Glu Val Lys Pro Asp Leu
                560                 565                 570

Ser Pro Ala Asp Ile Lys Thr Thr Leu Met Asn Thr Ala Asn Pro Met
            575                 580                 585

Thr Leu Asp Tyr Ser Val Phe Glu Ile Gly Ala Gly Gln Ile Asp Gln
        590                 595                 600

Arg Leu Leu Leu Leu Ser Phe Asp His Val Ser
    605                 610

<210> SEQ ID NO 3
<211> LENGTH: 828
<212> TYPE: DNA
<213> ORGANISM: Bacillus sp. P 203
<220> FEATURE:
<221> NAME/KEY: CDS
<222> LOCATION: (1)..(828)
<223> OTHER INFORMATION: carbonic anhydrase
<220> FEATURE:
<221> NAME/KEY: sig_peptide
<222> LOCATION: (1)..(87)
<220> FEATURE:
<221> NAME/KEY: mat_peptide
<222> LOCATION: (88)..(828)

<400> SEQUENCE: 3 atg aga aaa aca aac gtt cta ctg aaa tca act atg att aca aca cta       48
Met Arg Lys Thr Asn Val Leu Leu Lys Ser Thr Met Ile Thr Thr Leu
            -25                 -20                 -15 tta cta tca agt acg cta cta gta acc act ccg atc tat gca cac act       96
Leu Leu Ser Ser Thr Leu Leu Val Thr Thr Pro Ile Tyr Ala His Thr
        -10                  -5                  -1   1 gaa acc cag caa ctt tcc tac aag act ctt aat gat ttg cta acg gaa      144
Glu Thr Gln Gln Leu Ser Tyr Lys Thr Leu Asn Asp Leu Leu Thr Glu
        5                   10                  15 gat gga cac agt ggt tgg tct tat tcc ggt cta act ggt cct gag tat      192
Asp Gly His Ser Gly Trp Ser Tyr Ser Gly Leu Thr Gly Pro Glu Tyr
20                  25                  30                  35 tgg gga gag tta aat gaa gac tac aag gcc tgc tct aaa ggg gag gaa      240
Trp Gly Glu Leu Asn Glu Asp Tyr Lys Ala Cys Ser Lys Gly Glu Glu
                40                  45                  50 caa tca cct atc gct tta caa aat gaa gat atc gat aat gaa aag tgg      288
Gln Ser Pro Ile Ala Leu Gln Asn Glu Asp Ile Asp Asn Glu Lys Trp
            55                  60                  65 tct ttc gat cta gac tat gaa gaa act gag ttt tca att gaa aac aat      336
Ser Phe Asp Leu Asp Tyr Glu Glu Thr Glu Phe Ser Ile Glu Asn Asn
        70                  75                  80 ggc cat aca atc caa gcg aat gta gaa ggt tca tca tct aat acg tta      384
Gly His Thr Ile Gln Ala Asn Val Glu Gly Ser Ser Ser Asn Thr Leu
    85                  90                  95 ctt tta aat gat act gaa tat aac ctt gtc caa ttt cat ttc cat tca      432
Leu Leu Asn Asp Thr Glu Tyr Asn Leu Val Gln Phe His Phe His Ser
100                 105                 110                 115
```

```
cca agt gag cac acc tta gat gac gaa tac ttt gag atg gaa gta cat    480
Pro Ser Glu His Thr Leu Asp Asp Glu Tyr Phe Glu Met Glu Val His
            120                 125                 130 ttg gtg cat caa gat gaa cat gca aat tta gct gtt cta ggt gtc tta    528
Leu Val His Gln Asp Glu His Ala Asn Leu Ala Val Leu Gly Val Leu
        135                 140                 145 att gaa gaa ggc gaa cag aat gag acg ctt aca gat atg tgg gaa cta    576
Ile Glu Glu Gly Glu Gln Asn Glu Thr Leu Thr Asp Met Trp Glu Leu
    150                 155                 160 atg cct ggg cag caa ggt gaa gct gct gaa aga att act ctt aac cca    624
Met Pro Gly Gln Gln Gly Glu Ala Ala Glu Arg Ile Thr Leu Asn Pro
165                 170                 175 tct gaa tta gtg cct agt gat cta tca aca ttc caa tat gat ggt tcc    672
Ser Glu Leu Val Pro Ser Asp Leu Ser Thr Phe Gln Tyr Asp Gly Ser
180                 185                 190                 195 ctt act act cca cct tgc tca gaa gat gtg aaa tgg agt gtg agt gat    720
Leu Thr Thr Pro Pro Cys Ser Glu Asp Val Lys Trp Ser Val Ser Asp
            200                 205                 210 tcg aca att agc cta tct cct gaa cag ctc gag gca ttt caa gac cta    768
Ser Thr Ile Ser Leu Ser Pro Glu Gln Leu Glu Ala Phe Gln Asp Leu
        215                 220                 225 tac cca aat aac tat cgc cct att caa gac tta ggt aat aga gaa gtt    816
Tyr Pro Asn Asn Tyr Arg Pro Ile Gln Asp Leu Gly Asn Arg Glu Val
    230                 235                 240 gga ttt cac tat                                                    828
Gly Phe His Tyr
    245

<210> SEQ ID NO 4
<211> LENGTH: 276
<212> TYPE: PRT
<213> ORGANISM: Bacillus sp. P 203

<400> SEQUENCE: 4

Met Arg Lys Thr Asn Val Leu Leu Lys Ser Thr Met Ile Thr Thr Leu
                -25                 -20                 -15

Leu Leu Ser Ser Thr Leu Leu Val Thr Thr Pro Ile Tyr Ala His Thr
        -10                  -5                 -1   1

Glu Thr Gln Gln Leu Ser Tyr Lys Thr Leu Asn Asp Leu Leu Thr Glu
    5                   10                  15

Asp Gly His Ser Gly Trp Ser Tyr Ser Gly Leu Thr Gly Pro Glu Tyr
20                  25                  30                  35

Trp Gly Glu Leu Asn Glu Asp Tyr Lys Ala Cys Ser Lys Gly Glu Glu
            40                  45                  50

Gln Ser Pro Ile Ala Leu Gln Asn Glu Asp Ile Asp Asn Glu Lys Trp
        55                  60                  65

Ser Phe Asp Leu Asp Tyr Glu Glu Thr Glu Phe Ser Ile Glu Asn Asn
    70                  75                  80

Gly His Thr Ile Gln Ala Asn Val Glu Gly Ser Ser Ser Asn Thr Leu
85                  90                  95

Leu Leu Asn Asp Thr Glu Tyr Asn Leu Val Gln Phe His Phe His Ser
100                 105                 110                 115

Pro Ser Glu His Thr Leu Asp Asp Glu Tyr Phe Glu Met Glu Val His
            120                 125                 130

Leu Val His Gln Asp Glu His Ala Asn Leu Ala Val Leu Gly Val Leu
        135                 140                 145

Ile Glu Glu Gly Glu Gln Asn Glu Thr Leu Thr Asp Met Trp Glu Leu
    150                 155                 160
```

-continued

```
Met Pro Gly Gln Gln Gly Glu Ala Ala Glu Arg Ile Thr Leu Asn Pro
    165                 170                 175

Ser Glu Leu Val Pro Ser Asp Leu Ser Thr Phe Gln Tyr Asp Gly Ser
180                 185                 190                 195

Leu Thr Thr Pro Pro Cys Ser Glu Asp Val Lys Trp Ser Val Ser Asp
                    200                 205                 210

Ser Thr Ile Ser Leu Ser Pro Glu Gln Leu Glu Ala Phe Gln Asp Leu
            215                 220                 225

Tyr Pro Asn Asn Tyr Arg Pro Ile Gln Asp Leu Gly Asn Arg Glu Val
        230                 235                 240

Gly Phe His Tyr
        245

<210> SEQ ID NO 5
<211> LENGTH: 702
<212> TYPE: DNA
<213> ORGANISM: Bacillus sp. P203
<220> FEATURE:
<221> NAME/KEY: CDS
<222> LOCATION: (1)..(702)
<223> OTHER INFORMATION: carbonic anhydrase
<220> FEATURE:
<221> NAME/KEY: sig_peptide
<222> LOCATION: (1)..(90)
<220> FEATURE:
<221> NAME/KEY: mat_peptide
<222> LOCATION: (91)..(702)

<400> SEQUENCE: 5
```

| | | |
|---|---|---|
| ttg tca aaa atg aag aca ctt aga aaa ttg tca ttg tat gct gca ttt<br>Leu Ser Lys Met Lys Thr Leu Arg Lys Leu Ser Leu Tyr Ala Ala Phe<br>-30                  -25                  -20                  -15 | 48 |
| aca ctt tca agc agc tcg atg gtc acc gct cct ctc ttt gca cag aca<br>Thr Leu Ser Ser Ser Ser Met Val Thr Ala Pro Leu Phe Ala Gln Thr<br>                  -10                  -5                  -1  1 | 96 |
| gat aca cat caa cca ctt atc ccg tat cac tca ctc cac ctc ttg cta<br>Asp Thr His Gln Pro Leu Ile Pro Tyr His Ser Leu His Leu Leu Leu<br>        5                  10                  15 | 144 |
| cat tct aat gag aaa gaa ggc tgg tct tat tct ggc tca act ggc ccg<br>His Ser Asn Glu Lys Glu Gly Trp Ser Tyr Ser Gly Ser Thr Gly Pro<br>20                  25                  30 | 192 |
| cag ttc tgg gca gac cta cat gat gaa tac ata gca tgc tca caa gga<br>Gln Phe Trp Ala Asp Leu His Asp Glu Tyr Ile Ala Cys Ser Gln Gly<br>35                  40                  45                  50 | 240 |
| aaa gaa caa tcg cct gta gcc tta cat aat gaa gac gca tca gat gaa<br>Lys Glu Gln Ser Pro Val Ala Leu His Asn Glu Asp Ala Ser Asp Glu<br>                  55                  60                  65 | 288 |
| gga aaa tgg tca tta gat ctt gac tat aac gaa aca gat ttc tcc att<br>Gly Lys Trp Ser Leu Asp Leu Asp Tyr Asn Glu Thr Asp Phe Ser Ile<br>        70                  75                  80 | 336 |
| gag aat aac ggt cat acc att caa gca aat gta ggt gat cat tca tca<br>Glu Asn Asn Gly His Thr Ile Gln Ala Asn Val Gly Asp His Ser Ser<br>              85                  90                  95 | 384 |
| aat aaa ttg att gta aat gga acc gat tac aag ttg gcg cag ttc cat<br>Asn Lys Leu Ile Val Asn Gly Thr Asp Tyr Lys Leu Ala Gln Phe His<br>100                  105                  110 | 432 |
| ttc cat tct caa agt gag cat acc tta gac gat gat tat tac gag atg<br>Phe His Ser Gln Ser Glu His Thr Leu Asp Asp Asp Tyr Tyr Glu Met<br>115                  120                  125                  130 | 480 |
| gaa ctt cat tta gtt cat cag gat gag gaa gat aac ttg gcc gtc tta<br>Glu Leu His Leu Val His Gln Asp Glu Glu Asp Asn Leu Ala Val Leu<br>                  135                  140                  145 | 528 |

```
gga gtt cta att gag gaa gga gaa aag aac gag act cta gca aac atg    576
Gly Val Leu Ile Glu Glu Gly Glu Lys Asn Glu Thr Leu Ala Asn Met
            150                 155                 160 tgg gat gtg ata ccc gaa act gaa gga gaa gcc gat gaa acc att tct    624
Trp Asp Val Ile Pro Glu Thr Glu Gly Glu Ala Asp Glu Thr Ile Ser
        165                 170                 175 ctt aat ccc tca gaa cta gta cct aaa gat cca cta gtg tcg acc tgc    672
Leu Asn Pro Ser Glu Leu Val Pro Lys Asp Pro Leu Val Ser Thr Cys
    180                 185                 190 agg cgc gcg agc tcc agc ttt tgt tcc ctt                            702
Arg Arg Ala Ser Ser Ser Phe Cys Ser Leu
195                 200
```

<210> SEQ ID NO 6
<211> LENGTH: 234
<212> TYPE: PRT
<213> ORGANISM: Bacillus sp. P203

<400> SEQUENCE: 6

```
Leu Ser Lys Met Lys Thr Leu Arg Lys Leu Ser Leu Tyr Ala Ala Phe
-30                 -25                 -20                 -15

Thr Leu Ser Ser Ser Ser Met Val Thr Ala Pro Leu Phe Ala Gln Thr
                -10                 -5                  -1  1

Asp Thr His Gln Pro Leu Ile Pro Tyr His Ser Leu His Leu Leu Leu
            5                   10                  15

His Ser Asn Glu Lys Glu Gly Trp Ser Tyr Ser Gly Ser Thr Gly Pro
        20                  25                  30

Gln Phe Trp Ala Asp Leu His Asp Glu Tyr Ile Ala Cys Ser Gln Gly
35                  40                  45                  50

Lys Glu Gln Ser Pro Val Ala Leu His Asn Gly Asp Ala Ser Asp Glu
                55                  60                  65

Gly Lys Trp Ser Leu Asp Leu Asp Tyr Asn Glu Thr Asp Phe Ser Ile
            70                  75                  80

Glu Asn Asn Gly His Thr Ile Gln Ala Asn Val Gly Asp His Ser Ser
        85                  90                  95

Asn Lys Leu Ile Val Asn Gly Thr Asp Tyr Lys Leu Ala Gln Phe His
100                 105                 110

Phe His Ser Gln Ser Glu His Thr Leu Asp Asp Tyr Tyr Glu Met
115                 120                 125                 130

Glu Leu His Leu Val His Gln Asp Glu Asp Asn Leu Ala Val Leu
                135                 140                 145

Gly Val Leu Ile Glu Glu Gly Glu Lys Asn Glu Thr Leu Ala Asn Met
            150                 155                 160

Trp Asp Val Ile Pro Glu Thr Glu Gly Glu Ala Asp Glu Thr Ile Ser
        165                 170                 175

Leu Asn Pro Ser Glu Leu Val Pro Lys Asp Pro Leu Val Ser Thr Cys
    180                 185                 190

Arg Arg Ala Ser Ser Ser Phe Cys Ser Leu
195                 200
```

<210> SEQ ID NO 7
<211> LENGTH: 1080
<212> TYPE: DNA
<213> ORGANISM: Bacillus sp. P203
<220> FEATURE:
<221> NAME/KEY: CDS
<222> LOCATION: (1)..(1080)
<223> OTHER INFORMATION: xylanase
<220> FEATURE:

<221> NAME/KEY: sig_peptide
<222> LOCATION: (1)..(72)
<220> FEATURE:
<221> NAME/KEY: mat_peptide
<222> LOCATION: (73)..(1080)

<400> SEQUENCE: 7

| | | | | | | | | | | | | | | | | |
|---|---|---|---|---|---|---|---|---|---|---|---|---|---|---|---|---|
| atg | att | atc | agg | agg | cat | atg | ttg | aat | aga | aaa | ttg | ttc | aag | gtt | tta | 48 |
| Met | Ile | Ile | Arg | Arg | His | Met | Leu | Asn | Arg | Lys | Leu | Phe | Lys | Val | Leu | |
| | -20 | | | | | -15 | | | | | -10 | | | | | |
| ggt | agt | ata | ctt | atc | att | tct | gct | ggg | gtg | tat | ggt | tgg | atg | aag | ata | 96 |
| Gly | Ser | Ile | Leu | Ile | Ile | Ser | Ala | Gly | Val | Tyr | Gly | Trp | Met | Lys | Ile | |
| | -5 | | | | | -1 | 1 | | | | 5 | | | | | |
| cag | gat | caa | cat | aca | ata | cga | tca | atg | gct | gaa | gat | gaa | cag | atg | ttg | 144 |
| Gln | Asp | Gln | His | Thr | Ile | Arg | Ser | Met | Ala | Glu | Asp | Glu | Gln | Met | Leu | |
| | 10 | | | | 15 | | | | | 20 | | | | | | |
| ttt | ggc | aca | gct | atg | cgc | tat | cag | cca | ttt | tca | gat | gat | tcg | ggc | tat | 192 |
| Phe | Gly | Thr | Ala | Met | Arg | Tyr | Gln | Pro | Phe | Ser | Asp | Asp | Ser | Gly | Tyr | |
| 25 | | | | 30 | | | | | 35 | | | | | 40 | | |
| cga | gag | ttg | att | aaa | aat | gag | ttt | aat | gca | gtg | acc | att | gaa | aat | gaa | 240 |
| Arg | Glu | Leu | Ile | Lys | Asn | Glu | Phe | Asn | Ala | Val | Thr | Ile | Glu | Asn | Glu | |
| | | | | 45 | | | | | 50 | | | | | 55 | | |
| atg | aaa | atg | gaa | cta | gtt | atg | cct | gaa | cga | ggc | aag | tat | gat | ttc | agt | 288 |
| Met | Lys | Met | Glu | Leu | Val | Met | Pro | Glu | Arg | Gly | Lys | Tyr | Asp | Phe | Ser | |
| | | 60 | | | | | 65 | | | | | 70 | | | | |
| caa | gca | gat | gag | atg | gtg | caa | ttt | gct | gat | gaa | aat | gga | ctt | caa | gta | 336 |
| Gln | Ala | Asp | Glu | Met | Val | Gln | Phe | Ala | Asp | Glu | Asn | Gly | Leu | Gln | Val | |
| | | 75 | | | | | 80 | | | | | 85 | | | | |
| aga | ggc | cac | act | ctc | gta | tgg | gaa | cgt | atc | cct | tgg | tgg | ctc | gat | cag | 384 |
| Arg | Gly | His | Thr | Leu | Val | Trp | Glu | Arg | Ile | Pro | Trp | Trp | Leu | Asp | Gln | |
| | 90 | | | | | 95 | | | | | 100 | | | | | |
| ggc | aat | ttt | acc | aga | gat | gaa | ata | acc | aac | cta | tta | aaa | gag | tat | gtc | 432 |
| Gly | Asn | Phe | Thr | Arg | Asp | Glu | Ile | Thr | Asn | Leu | Leu | Lys | Glu | Tyr | Val | |
| 105 | | | | | 110 | | | | | 115 | | | | | 120 | |
| caa | aca | acg | gta | aag | caa | tac | caa | ggt | cga | atc | tat | gcc | tgg | gat | gta | 480 |
| Gln | Thr | Thr | Val | Lys | Gln | Tyr | Gln | Gly | Arg | Ile | Tyr | Ala | Trp | Asp | Val | |
| | | | | 125 | | | | | 130 | | | | | 135 | | |
| gta | aat | gaa | gcg | ttt | gat | aac | aaa | gga | aat | ctg | aaa | gag | aac | ttc | tgg | 528 |
| Val | Asn | Glu | Ala | Phe | Asp | Asn | Lys | Gly | Asn | Leu | Lys | Glu | Asn | Phe | Trp | |
| | | | 140 | | | | | 145 | | | | | 150 | | | |
| ctg | cag | cat | atc | ggt | tca | gat | tac | att | gaa | ctt | gct | ttt | cga | tgg | gca | 576 |
| Leu | Gln | His | Ile | Gly | Ser | Asp | Tyr | Ile | Glu | Leu | Ala | Phe | Arg | Trp | Ala | |
| | | 155 | | | | | 160 | | | | | 165 | | | | |
| aaa | gaa | gca | gat | cca | gat | gct | tta | ctg | ttt | tat | aac | gat | tat | gag | aac | 624 |
| Lys | Glu | Ala | Asp | Pro | Asp | Ala | Leu | Leu | Phe | Tyr | Asn | Asp | Tyr | Glu | Asn | |
| | 170 | | | | | 175 | | | | | 180 | | | | | |
| gaa | gta | ccc | tct | gct | aaa | act | gaa | gca | acg | ata | aaa | tgg | ttg | tca | gag | 672 |
| Glu | Val | Pro | Ser | Ala | Lys | Thr | Glu | Ala | Thr | Ile | Lys | Trp | Leu | Ser | Glu | |
| 185 | | | | | 190 | | | | | 195 | | | | | 200 | |
| ctg | cgc | caa | aag | gga | gta | cca | ata | gat | ggc | atc | ggc | atg | caa | atg | cat | 720 |
| Leu | Arg | Gln | Lys | Gly | Val | Pro | Ile | Asp | Gly | Ile | Gly | Met | Gln | Met | His | |
| | | | | 205 | | | | | 210 | | | | | 215 | | |
| tta | gat | att | gca | aat | gat | ttt | cat | gtt | gat | cag | gta | caa | aat | gta | atg | 768 |
| Leu | Asp | Ile | Ala | Asn | Asp | Phe | His | Val | Asp | Gln | Val | Gln | Asn | Val | Met | |
| | | | 220 | | | | | 225 | | | | | 230 | | | |
| aat | caa | atg | gag | cag | gaa | gga | ttt | tta | gta | cat | att | aca | gaa | cta | gac | 816 |
| Asn | Gln | Met | Glu | Gln | Glu | Gly | Phe | Leu | Val | His | Ile | Thr | Glu | Leu | Asp | |
| | | 235 | | | | | 240 | | | | | 245 | | | | |
| ata | aag | ctc | caa | cat | agt | ggg | gag | gat | ctg | gag | acg | aaa | caa | cag | cta | 864 |
| Ile | Lys | Leu | Gln | His | Ser | Gly | Glu | Asp | Leu | Glu | Thr | Lys | Gln | Gln | Leu | |
| | 250 | | | | | 255 | | | | | 260 | | | | | |

```
cag gca gaa cga tat gca gaa ata atg aag gtc tgt tta cag caa gca       912
Gln Ala Glu Arg Tyr Ala Glu Ile Met Lys Val Cys Leu Gln Gln Ala
265                 270                 275                 280 aca tgc gac tcc ttc acg gtg tgg ggt gcg gct gat cca tat agt tgg       960
Thr Cys Asp Ser Phe Thr Val Trp Gly Ala Ala Asp Pro Tyr Ser Trp
                285                 290                 295 att ggg ttt aca gag gag cca gga gcg agt gtt gcc tac cca ctt ctt      1008
Ile Gly Phe Thr Glu Glu Pro Gly Ala Ser Val Ala Tyr Pro Leu Leu
                300                 305                 310 ttt gat gat aaa ttg aaa cgg aag ccg gca tat aag gcg att aaa gct      1056
Phe Asp Asp Lys Leu Lys Arg Lys Pro Ala Tyr Lys Ala Ile Lys Ala
                315                 320                 325 ata ttt aaa gaa gat att cgt aaa                                      1080
Ile Phe Lys Glu Asp Ile Arg Lys
330                 335

<210> SEQ ID NO 8
<211> LENGTH: 360
<212> TYPE: PRT
<213> ORGANISM: Bacillus sp. P203

<400> SEQUENCE: 8

Met Ile Ile Arg Arg His Met Leu Asn Arg Lys Leu Phe Lys Val Leu
                -20                 -15                 -10

Gly Ser Ile Leu Ile Ser Ala Gly Val Tyr Gly Trp Met Lys Ile
            -5              -1   1               5

Gln Asp Gln His Thr Ile Arg Ser Met Ala Glu Asp Glu Gln Met Leu
        10                  15                  20

Phe Gly Thr Ala Met Arg Tyr Gln Pro Phe Ser Asp Ser Gly Tyr
25                  30                  35                  40

Arg Glu Leu Ile Lys Asn Glu Phe Asn Ala Val Thr Ile Glu Asn
                45                  50                  55

Met Lys Met Glu Leu Val Met Pro Glu Arg Gly Lys Tyr Asp Phe Ser
            60                  65                  70

Gln Ala Asp Glu Met Val Gln Phe Ala Asp Glu Asn Gly Leu Gln Val
        75                  80                  85

Arg Gly His Thr Leu Val Trp Glu Arg Ile Pro Trp Trp Leu Asp Gln
    90                  95                  100

Gly Asn Phe Thr Arg Asp Glu Ile Thr Asn Leu Leu Lys Glu Tyr Val
105                 110                 115                 120

Gln Thr Thr Val Lys Gln Tyr Gln Gly Arg Ile Tyr Ala Trp Asp Val
                125                 130                 135

Val Asn Glu Ala Phe Asp Asn Lys Gly Asn Leu Lys Glu Asn Phe Trp
            140                 145                 150

Leu Gln His Ile Gly Ser Asp Tyr Ile Glu Leu Ala Phe Arg Trp Ala
        155                 160                 165

Lys Glu Ala Asp Pro Asp Ala Leu Leu Phe Tyr Asn Asp Tyr Glu Asn
    170                 175                 180

Glu Val Pro Ser Ala Lys Thr Glu Ala Thr Ile Lys Trp Leu Ser Glu
185                 190                 195                 200

Leu Arg Gln Lys Gly Val Pro Ile Asp Gly Ile Gly Met Gln Met His
                205                 210                 215

Leu Asp Ile Ala Asn Asp Phe His Val Asp Gln Val Gln Asn Val Met
            220                 225                 230

Asn Gln Met Glu Gln Glu Gly Phe Leu Val His Ile Thr Glu Leu Asp
        235                 240                 245

Ile Lys Leu Gln His Ser Gly Glu Asp Leu Glu Thr Lys Gln Gln Leu
```

```
                   250                    255                    260
Gln Ala Glu Arg Tyr Ala Glu Ile Met Lys Val Cys Leu Gln Gln Ala
265                    270                    275                    280

Thr Cys Asp Ser Phe Thr Val Trp Gly Ala Ala Asp Pro Tyr Ser Trp
                   285                    290                    295

Ile Gly Phe Thr Glu Glu Pro Gly Ala Ser Val Ala Tyr Pro Leu Leu
                   300                    305                    310

Phe Asp Asp Lys Leu Lys Arg Lys Pro Ala Tyr Lys Ala Ile Lys Ala
                   315                    320                    325

Ile Phe Lys Glu Asp Ile Arg Lys
                   330                    335

<210> SEQ ID NO 9
<211> LENGTH: 2712
<212> TYPE: DNA
<213> ORGANISM: Bacillus sp. P203
<220> FEATURE:
<221> NAME/KEY: CDS
<222> LOCATION: (1)..(2712)
<223> OTHER INFORMATION: Rhamnogalacturonan lyase
<220> FEATURE:
<221> NAME/KEY: sig_peptide
<222> LOCATION: (1)..(87)
<220> FEATURE:
<221> NAME/KEY: mat_peptide
<222> LOCATION: (88)..(2712)

<400> SEQUENCE: 9 atg ttc aaa agg cag ggg aaa gga att ctt ttt ggg tta ctt gtt gtg     48
Met Phe Lys Arg Gln Gly Lys Gly Ile Leu Phe Gly Leu Leu Val Val
                -25                    -20                    -15 gtt ttg gtc tgt gct aac atg tcc gga caa gct att gct aaa aaa caa     96
Val Leu Val Cys Ala Asn Met Ser Gly Gln Ala Ile Ala Lys Lys Gln
         -10                     -5                     -1  1 gaa aag aaa gat ctc act gta act gaa gtg act gat tca agt gtg tca    144
Glu Lys Lys Asp Leu Thr Val Thr Glu Val Thr Asp Ser Ser Val Ser
             5                      10                     15 ttg tct tgg aag cag gta aaa ggg gca gat tcg tat aac gtg tat tgg    192
Leu Ser Trp Lys Gln Val Lys Gly Ala Asp Ser Tyr Asn Val Tyr Trp
 20                     25                     30                     35 gca gat aaa gat acg gag aat atg gaa tat cga cta ctt gat aac gtt    240
Ala Asp Lys Asp Thr Glu Asn Met Glu Tyr Arg Leu Leu Asp Asn Val
                 40                     45                     50 tca gag act acc tac acc tac gaa cgt tca acg cat atc cct cat tat    288
Ser Glu Thr Thr Tyr Thr Tyr Glu Arg Ser Thr His Ile Pro His Tyr
             55                     60                     65 ttt aag att gtt cca gta aca aat gga gaa gaa ggt gaa ttt tca aat    336
Phe Lys Ile Val Pro Val Thr Asn Gly Glu Glu Gly Glu Phe Ser Asn
 70                     75                     80 act gtt caa act gat att aaa aaa ata ttt gac caa cag ctt gag gat    384
Thr Val Gln Thr Asp Ile Lys Lys Ile Phe Asp Gln Gln Leu Glu Asp
 85                     90                     95 ttg gac cgt gga gtg gtc gct gtc tca aca tct gaa ggt gta ttt tta    432
Leu Asp Arg Gly Val Val Ala Val Ser Thr Ser Glu Gly Val Phe Leu
100                    105                    110                    115 agc tgg agg ctg tta aag cag gaa gta gat ggt cat tct gag aca ggc    480
Ser Trp Arg Leu Leu Lys Gln Glu Val Asp Gly His Ser Glu Thr Gly
                120                    125                    130 tta acc ggt gtt gat ttt tat gtt tac cga gat gga agc aaa att gca    528
Leu Thr Gly Val Asp Phe Tyr Val Tyr Arg Asp Gly Ser Lys Ile Ala
             135                    140                    145 gaa gtg aca gac agc aca aat tac ttg gac gaa gaa gga aca gcc agt    576
```

-continued

| | | |
|---|---|---|
| Glu Val Thr Asp Ser Thr Asn Tyr Leu Asp Glu Gly Thr Ala Ser<br>        150                        155                  160 | | |
| ttt gaa tat acg att aga gcc gtg gat cat ggt aag gag ctg gat gaa<br>Phe Glu Tyr Thr Ile Arg Ala Val Asp His Gly Lys Glu Leu Asp Glu<br>165                     170                   175 | 624 | |
| agt gag cca gta agt ccg tgg gca gac ggt tat tat gat ttg ccg ttg<br>Ser Glu Pro Val Ser Pro Trp Ala Asp Gly Tyr Tyr Asp Leu Pro Leu<br>180                     185                    190             195 | 672 | |
| caa aaa cca gcg gat ggg gta act cca gct ggc gag tcc tat acg tac<br>Gln Lys Pro Ala Asp Gly Val Thr Pro Ala Gly Glu Ser Tyr Thr Tyr<br>                  200                    205                    210 | 720 | |
| cat gca aat gat atg agt gta ggg gat gtt gat ggc gat gga caa tac<br>His Ala Asn Asp Met Ser Val Gly Asp Val Asp Gly Asp Gly Gln Tyr<br>              215                   220                    225 | 768 | |
| gaa ttt atc gtt aaa tgg gat cca tca aat tca aag gac gtc tct caa<br>Glu Phe Ile Val Lys Trp Asp Pro Ser Asn Ser Lys Asp Val Ser Gln<br>        230                    235                    240 | 816 | |
| aaa ggc tac aca gga aat acg tat att gac acg tat acg ttt gaa gga<br>Lys Gly Tyr Thr Gly Asn Thr Tyr Ile Asp Thr Tyr Thr Phe Glu Gly<br>245                     250                    255 | 864 | |
| gag tta ctt tat cga att gat tta ggt gta aat gtt cgc tct gga gca<br>Glu Leu Leu Tyr Arg Ile Asp Leu Gly Val Asn Val Arg Ser Gly Ala<br>260                     265                    270             275 | 912 | |
| cat tat act caa ttt tta gtc tat gac ttt gat gga gat gga aaa gcg<br>His Tyr Thr Gln Phe Leu Val Tyr Asp Phe Asp Gly Asp Gly Lys Ala<br>              280                   285                    290 | 960 | |
| gaa atc atg ttt aag aca gca cct gga aca aag ata cta aca ttt aat<br>Glu Ile Met Phe Lys Thr Ala Pro Gly Thr Lys Ile Leu Thr Phe Asn<br>                  295                    300                  305 | 1008 | |
| ggt aat gga gag att gaa acc gaa gag tac atc acg atg cca gaa gag<br>Gly Asn Gly Glu Ile Glu Thr Glu Glu Tyr Ile Thr Met Pro Glu Glu<br>        310                    315                    320 | 1056 | |
| gat cta tct aaa ggc tat agt cat gaa gat gac tac cga atg agt tca<br>Asp Leu Ser Lys Gly Tyr Ser His Glu Asp Asp Tyr Arg Met Ser Ser<br>325                     330                    335 | 1104 | |
| gag gat tat tat cag cat atc gtt cag atg ttt atg gaa tgg cat gaa<br>Glu Asp Tyr Tyr Gln His Ile Val Gln Met Phe Met Glu Trp His Glu<br>340                     345                    350             355 | 1152 | |
| cat gag gag gta gtg gat ggt aat tgg cca gca aca ctt gaa gag agt<br>His Glu Glu Val Val Asp Gly Asn Trp Pro Ala Thr Leu Glu Glu Ser<br>                  360                    365                  370 | 1200 | |
| ttt ggt att gac gtt caa tat gaa tat cca ctt tct aaa gag gat gct<br>Phe Gly Ile Asp Val Gln Tyr Glu Tyr Pro Leu Ser Lys Glu Asp Ala<br>                  375                    380                  385 | 1248 | |
| gag tcg tta gct gat tat ttt atg gac gag tat gcg cct tct cgc agc<br>Glu Ser Leu Ala Asp Tyr Phe Met Asp Glu Tyr Ala Pro Ser Arg Ser<br>390                     395                    400 | 1296 | |
| ggg cgt aat gac cta cga gac ttt gaa ggc ttt att gtt gaa gga cca<br>Gly Arg Asn Asp Leu Arg Asp Phe Glu Gly Phe Ile Val Glu Gly Pro<br>405                     410                    415 | 1344 | |
| gaa tat tta acc gta ttt gaa gga gag aca ggc aag gag tta gaa acc<br>Glu Tyr Leu Thr Val Phe Glu Gly Glu Thr Gly Lys Glu Leu Glu Thr<br>420                     425                    430             435 | 1392 | |
| att cat tat aag cct gga aga agc gat gat gga ttg atg tgg gga gat<br>Ile His Tyr Lys Pro Gly Arg Ser Asp Asp Gly Leu Met Trp Gly Asp<br>                  440                    445                  450 | 1440 | |
| tat gcg atg gct cgc att gag cct gga aac cgc gtt gat cgt ttt cta<br>Tyr Ala Met Ala Arg Ile Glu Pro Gly Asn Arg Val Asp Arg Phe Leu<br>455                     460                    465 | 1488 | |
| gca ggg gtc gcc tac cta gat ggt gag aat cca tac gct gta ttt gct | 1536 | |

```
                Ala Gly Val Ala Tyr Leu Asp Gly Glu Asn Pro Tyr Ala Val Phe Ala
                            470                 475                 480 aga gga tac tac aca aga aca aca ctt gtt tca tat gat tgg gac gga          1584
Arg Gly Tyr Tyr Thr Arg Thr Thr Leu Val Ser Tyr Asp Trp Asp Gly
            485                 490                 495 cag agc tta aat gaa cac tgg tac gta gat agt ggt tgg aca cca atg          1632
Gln Ser Leu Asn Glu His Trp Tyr Val Asp Ser Gly Trp Thr Pro Met
500                 505                 510                 515 tct aat cca ttt aat gat ggt cca cat gga gta gat ggg act gac gaa          1680
Ser Asn Pro Phe Asn Asp Gly Pro His Gly Val Asp Gly Thr Asp Glu
                520                 525                 530 gaa ttt gga aca att aca aca caa ggt gct cac tct ttg agt gtt gct          1728
Glu Phe Gly Thr Ile Thr Thr Gln Gly Ala His Ser Leu Ser Val Ala
            535                 540                 545 gat gtt gat ggt gat ggg aag cac gaa att atc tac ggt gga gct acg          1776
Asp Val Asp Gly Asp Gly Lys His Glu Ile Ile Tyr Gly Gly Ala Thr
        550                 555                 560 att gac cac gat ggc tcc ttg tta tat agc tcc ttt gac aca atg cca          1824
Ile Asp His Asp Gly Ser Leu Leu Tyr Ser Ser Phe Asp Thr Met Pro
565                 570                 575 cca gga agt gct aac cct gga gaa gaa gca aga ctt gga cac ggg gat          1872
Pro Gly Ser Ala Asn Pro Gly Glu Glu Ala Arg Leu Gly His Gly Asp
580                 585                 590                 595 gcg ctt cat gta gcc gat gtg atc ctg ata gac cag gtt tgg aga gct          1920
Ala Leu His Val Ala Asp Val Ile Leu Ile Asp Gln Val Trp Arg Ala
                600                 605                 610 tta tgg tat ttg aag gcg gtc aat ggg cgc ctt atg gat atg cct tac          1968
Leu Trp Tyr Leu Lys Ala Val Asn Gly Arg Leu Met Asp Met Pro Tyr
            615                 620                 625 gtg atg ctg aat ctg gag atg tgt tat atg gcg gga tac ggt cga gat          2016
Val Met Leu Asn Leu Glu Met Cys Tyr Met Ala Gly Tyr Gly Arg Asp
        630                 635                 640 act ggt cgc ggt atg gtt ggt gat gtg aat cca gac aag cga ggc ctt          2064
Thr Gly Arg Gly Met Val Gly Asp Val Asn Pro Asp Lys Arg Gly Leu
645                 650                 655 gaa aca tgg gct gta gga cta tgg aca gct gac gga gag aaa ctc agt          2112
Glu Thr Trp Ala Val Gly Leu Trp Thr Ala Asp Gly Glu Lys Leu Ser
660                 665                 670                 675 gac agc atg ccg ggt aca aat ttt aat att aaa tgg tct gga gat tta          2160
Asp Ser Met Pro Gly Thr Asn Phe Asn Ile Lys Trp Ser Gly Asp Leu
                680                 685                 690 acc aca caa ata gtg aat ggt tcc att gat caa acg cct tcc att gat          2208
Thr Thr Gln Ile Val Asn Gly Ser Ile Asp Gln Thr Pro Ser Ile Asp
            695                 700                 705 gat tgg cag aaa gga cga tta ctt acg gca gaa ggc act aga acc aac          2256
Asp Trp Gln Lys Gly Arg Leu Leu Thr Ala Glu Gly Thr Arg Thr Asn
        710                 715                 720 aat tac aca aaa ggt aca cct tca ctc gtt gca gat gtg ttt ggg gat          2304
Asn Tyr Thr Lys Gly Thr Pro Ser Leu Val Ala Asp Val Phe Gly Asp
725                 730                 735 ttt aga gaa gag ttg cta gtt aga aca aca gat agc tca gcc ata cgt          2352
Phe Arg Glu Glu Leu Leu Val Arg Thr Thr Asp Ser Ser Ala Ile Arg
740                 745                 750                 755 atc tac aca agt aca gag gtc acg gag cat aag ctt tac aca ttg atg          2400
Ile Tyr Thr Ser Thr Glu Val Thr Glu His Lys Leu Tyr Thr Leu Met
                760                 765                 770 cat gat act caa tat cga aca ggc atc gca tgg caa aat gta acc tac          2448
His Asp Thr Gln Tyr Arg Thr Gly Ile Ala Trp Gln Asn Val Thr Tyr
            775                 780                 785 aac caa cca tcc tat ccg ggc ttt tat tat gca tct gat atg gat tgg          2496
```

-continued

```
Asn Gln Pro Ser Tyr Pro Gly Phe Tyr Tyr Ala Ser Asp Met Asp Trp
        790                 795                 800 gag tat gta cct gtt cca gtt gat caa cag aaa gat tct att aac tca    2544
Glu Tyr Val Pro Val Pro Val Asp Gln Gln Lys Asp Ser Ile Asn Ser
805                 810                 815 act aga aga tcc act agt gtc gac ctg cag gcg cgc gag ctc cag ctt    2592
Thr Arg Arg Ser Thr Ser Val Asp Leu Gln Ala Arg Glu Leu Gln Leu
820                 825                 830                 835 ttg ttc cct tta gtg agg gtt aat ttc gag ctt ggc gta atc aag gtc    2640
Leu Phe Pro Leu Val Arg Val Asn Phe Glu Leu Gly Val Ile Lys Val
            840                 845                 850 ata gct gtt tcc tgt gtg aaa ttg tta tcc gct cac aat tcc aca caa    2688
Ile Ala Val Ser Cys Val Lys Leu Leu Ser Ala His Asn Ser Thr Gln
            855                 860                 865 tat acg agc cgg aag tat aaa gtg                                    2712
Tyr Thr Ser Arg Lys Tyr Lys Val
            870                 875

<210> SEQ ID NO 10
<211> LENGTH: 904
<212> TYPE: PRT
<213> ORGANISM: Bacillus sp. P203

<400> SEQUENCE: 10

Met Phe Lys Arg Gln Gly Lys Gly Ile Leu Phe Gly Leu Leu Val Val
            -25                 -20                 -15

Val Leu Val Cys Ala Asn Met Ser Gly Gln Ala Ile Ala Lys Lys Gln
            -10                  -5          -1  1

Glu Lys Lys Asp Leu Thr Val Thr Glu Val Thr Asp Ser Ser Val Ser
5                   10                  15

Leu Ser Trp Lys Gln Val Lys Gly Ala Asp Ser Tyr Asn Val Tyr Trp
20                  25                  30                  35

Ala Asp Lys Asp Thr Glu Asn Met Glu Tyr Arg Leu Leu Asp Asn Val
                40                  45                  50

Ser Glu Thr Thr Tyr Thr Tyr Glu Arg Ser Thr His Ile Pro His Tyr
            55                  60                  65

Phe Lys Ile Val Pro Val Thr Asn Gly Glu Gly Glu Phe Ser Asn
        70                  75                  80

Thr Val Gln Thr Asp Ile Lys Lys Ile Phe Asp Gln Gln Leu Glu Asp
85                  90                  95

Leu Asp Arg Gly Val Val Ala Val Ser Thr Ser Glu Gly Val Phe Leu
100                 105                 110                 115

Ser Trp Arg Leu Leu Lys Gln Glu Val Asp Gly His Ser Glu Thr Gly
            120                 125                 130

Leu Thr Gly Val Asp Phe Tyr Val Tyr Arg Asp Gly Ser Lys Ile Ala
            135                 140                 145

Glu Val Thr Asp Ser Thr Asn Tyr Leu Asp Glu Glu Gly Thr Ala Ser
            150                 155                 160

Phe Glu Tyr Thr Ile Arg Ala Val Asp His Gly Lys Glu Leu Asp Glu
165                 170                 175

Ser Glu Pro Val Ser Pro Trp Ala Asp Gly Tyr Tyr Asp Leu Pro Leu
180                 185                 190                 195

Gln Lys Pro Ala Asp Gly Val Thr Pro Ala Gly Glu Ser Tyr Thr Tyr
                200                 205                 210

His Ala Asn Asp Met Ser Val Gly Asp Val Asp Gly Asp Gly Gln Tyr
            215                 220                 225

Glu Phe Ile Val Lys Trp Asp Pro Ser Asn Ser Lys Asp Val Ser Gln
```

```
                230                 235                 240
Lys Gly Tyr Thr Gly Asn Thr Tyr Ile Asp Thr Tyr Thr Phe Glu Gly
                245                 250                 255
Glu Leu Leu Tyr Arg Ile Asp Leu Gly Val Asn Val Arg Ser Gly Ala
260                 265                 270                 275
His Tyr Thr Gln Phe Leu Val Tyr Asp Phe Asp Gly Asp Gly Lys Ala
                    280                 285                 290
Glu Ile Met Phe Lys Thr Ala Pro Gly Thr Lys Ile Leu Thr Phe Asn
                295                 300                 305
Gly Asn Gly Glu Ile Glu Thr Glu Tyr Ile Thr Met Pro Glu Glu
                310                 315                 320
Asp Leu Ser Lys Gly Tyr Ser His Glu Asp Tyr Arg Met Ser Ser
    325                 330                 335
Glu Asp Tyr Tyr Gln His Ile Val Gln Met Phe Met Glu Trp His Glu
340                 345                 350                 355
His Glu Glu Val Val Asp Gly Asn Trp Pro Ala Thr Leu Glu Glu Ser
                    360                 365                 370
Phe Gly Ile Asp Val Gln Tyr Glu Tyr Pro Leu Ser Lys Glu Asp Ala
                375                 380                 385
Glu Ser Leu Ala Asp Tyr Phe Met Asp Glu Tyr Ala Pro Ser Arg Ser
    390                 395                 400
Gly Arg Asn Asp Leu Arg Asp Phe Glu Gly Phe Ile Val Glu Gly Pro
    405                 410                 415
Glu Tyr Leu Thr Val Phe Glu Gly Glu Thr Gly Lys Glu Leu Glu Thr
420                 425                 430                 435
Ile His Tyr Lys Pro Gly Arg Ser Asp Asp Gly Leu Met Trp Gly Asp
                    440                 445                 450
Tyr Ala Met Ala Arg Ile Glu Pro Gly Asn Arg Val Asp Arg Phe Leu
                455                 460                 465
Ala Gly Val Ala Tyr Leu Asp Gly Glu Asn Pro Tyr Ala Val Phe Ala
                470                 475                 480
Arg Gly Tyr Tyr Thr Arg Thr Thr Leu Val Ser Tyr Asp Trp Asp Gly
    485                 490                 495
Gln Ser Leu Asn Glu His Trp Tyr Val Asp Ser Gly Trp Thr Pro Met
500                 505                 510                 515
Ser Asn Pro Phe Asn Asp Gly Pro His Gly Val Asp Gly Thr Asp Glu
                    520                 525                 530
Glu Phe Gly Thr Ile Thr Thr Gln Gly Ala His Ser Leu Ser Val Ala
                535                 540                 545
Asp Val Asp Gly Asp Gly Lys His Glu Ile Ile Tyr Gly Gly Ala Thr
    550                 555                 560
Ile Asp His Asp Gly Ser Leu Leu Tyr Ser Ser Phe Asp Thr Met Pro
    565                 570                 575
Pro Gly Ser Ala Asn Pro Gly Glu Glu Ala Arg Leu Gly His Gly Asp
580                 585                 590                 595
Ala Leu His Val Ala Asp Val Ile Leu Ile Asp Gln Val Trp Arg Ala
                    600                 605                 610
Leu Trp Tyr Leu Lys Ala Val Asn Gly Arg Leu Met Asp Met Pro Tyr
                615                 620                 625
Val Met Leu Asn Leu Glu Met Cys Tyr Met Ala Gly Tyr Gly Arg Asp
        630                 635                 640
Thr Gly Arg Gly Met Val Gly Asp Val Asn Pro Asp Lys Arg Gly Leu
    645                 650                 655
```

-continued

```
Glu Thr Trp Ala Val Gly Leu Trp Thr Ala Asp Gly Glu Lys Leu Ser
660                 665                 670                 675

Asp Ser Met Pro Gly Thr Asn Phe Asn Ile Lys Trp Ser Gly Asp Leu
            680                 685                 690

Thr Thr Gln Ile Val Asn Gly Ser Ile Asp Gln Thr Pro Ser Ile Asp
        695                 700                 705

Asp Trp Gln Lys Gly Arg Leu Leu Thr Ala Glu Gly Thr Arg Thr Asn
    710                 715                 720

Asn Tyr Thr Lys Gly Thr Pro Ser Leu Val Ala Asp Val Phe Gly Asp
725                 730                 735

Phe Arg Glu Glu Leu Leu Val Arg Thr Thr Asp Ser Ser Ala Ile Arg
740                 745                 750                 755

Ile Tyr Thr Ser Thr Glu Val Thr Glu His Lys Leu Tyr Thr Leu Met
            760                 765                 770

His Asp Thr Gln Tyr Arg Thr Gly Ile Ala Trp Gln Asn Val Thr Tyr
        775                 780                 785

Asn Gln Pro Ser Tyr Pro Gly Phe Tyr Ala Ser Asp Met Asp Trp
    790                 795                 800

Glu Tyr Val Pro Val Pro Val Asp Gln Lys Asp Ser Ile Asn Ser
805                 810                 815

Thr Arg Arg Ser Thr Ser Val Asp Leu Gln Ala Arg Glu Leu Gln Leu
820                 825                 830                 835

Leu Phe Pro Leu Val Arg Val Asn Phe Glu Leu Gly Val Ile Lys Val
            840                 845                 850

Ile Ala Val Ser Cys Val Lys Leu Leu Ser Ala His Asn Ser Thr Gln
        855                 860                 865

Tyr Thr Ser Arg Lys Tyr Lys Val
        870                 875

<210> SEQ ID NO 11
<211> LENGTH: 1602
<212> TYPE: DNA
<213> ORGANISM: Bacillus sp. P203
<220> FEATURE:
<221> NAME/KEY: CDS
<222> LOCATION: (1)..(1602)
<223> OTHER INFORMATION: galactanase
<220> FEATURE:
<221> NAME/KEY: sig_peptide
<222> LOCATION: (1)..(93)
<220> FEATURE:
<221> NAME/KEY: mat_peptide
<222> LOCATION: (94)..(1602)

<400> SEQUENCE: 11 atg att caa atg aaa aga atg ttt ggt act tgt tta gct gtt gct gtc     48
Met Ile Gln Met Lys Arg Met Phe Gly Thr Cys Leu Ala Val Ala Val
    -30                 -25                 -20 tta ggt ata ccg act ata ggt gga cag gct ggc gta gca aac gca gcc     96
Leu Gly Ile Pro Thr Ile Gly Gly Gln Ala Gly Val Ala Asn Ala Ala
-15                 -10                 -5                 -1   1 tct gaa ccg gta caa tcc gaa cta ttc gta gag aag gta gag gga cta    144
Ser Glu Pro Val Gln Ser Glu Leu Phe Val Glu Lys Val Glu Gly Leu
            5                   10                  15 gat gaa gat ttt att aga ggg gta gat ata tcg agt gtg att gct atg    192
Asp Glu Asp Phe Ile Arg Gly Val Asp Ile Ser Ser Val Ile Ala Met
        20                  25                  30 gaa aat agc gga acg gtc tat tac aac gaa gaa ggg gaa gag caa gat    240
Glu Asn Ser Gly Thr Val Tyr Tyr Asn Glu Glu Gly Glu Glu Gln Asp
    35                  40                  45
```

| | | |
|---|---|---|
| gtg ttt cag act ttt aag gag gca gga gcc aat tac gtg cga gtg cgt<br>Val Phe Gln Thr Phe Lys Glu Ala Gly Ala Asn Tyr Val Arg Val Arg<br>50                     55                          60                    65 | | 288 |
| gta tgg aat gat cca tac gat gct gaa ggg aac agc tat ggc gga gga<br>Val Trp Asn Asp Pro Tyr Asp Ala Glu Gly Asn Ser Tyr Gly Gly Gly<br>                   70                        75                          80 | | 336 |
| aat aat gat cta gaa acg gcg att gaa att gga aaa cga gcc aca gaa<br>Asn Asn Asp Leu Glu Thr Ala Ile Glu Ile Gly Lys Arg Ala Thr Glu<br>                   85                        90                          95 | | 384 |
| aat ggg atg aaa cta tta gta gac ttc cat tac tcc gac ttt tgg gcg<br>Asn Gly Met Lys Leu Leu Val Asp Phe His Tyr Ser Asp Phe Trp Ala<br>       100                         105                        110 | | 432 |
| gac cca ggg aaa cag ttc ccc cct aaa gca tgg gag aat tta agt ctt<br>Asp Pro Gly Lys Gln Phe Pro Pro Lys Ala Trp Glu Asn Leu Ser Leu<br>115                     120                          125 | | 480 |
| gaa gag aaa aaa gct gag cta tat gac ttt acg aag gat agt tta gaa<br>Glu Glu Lys Lys Ala Glu Leu Tyr Asp Phe Thr Lys Asp Ser Leu Glu<br>130                     135                        140                    145 | | 528 |
| gaa atg ctt gct gaa gga ata cac att ggg atg gtt cag atc ggt aat<br>Glu Met Leu Ala Glu Gly Ile His Ile Gly Met Val Gln Ile Gly Asn<br>                   150                        155                        160 | | 576 |
| gaa aca aca aat ggg ctg gcc ggt gaa tat gat tgg tct aat atc acg<br>Glu Thr Thr Asn Gly Leu Ala Gly Glu Tyr Asp Trp Ser Asn Ile Thr<br>               165                        170                        175 | | 624 |
| tcg ttg atc aat gaa gga agt aag gcg gta agg gaa gtg gac gag gat<br>Ser Leu Ile Asn Glu Gly Ser Lys Ala Val Arg Glu Val Asp Glu Asp<br>    180                          185                        190 | | 672 |
| att ctc atc gct tta cac ttt aca aac cct gaa aga gaa ggg aga tac<br>Ile Leu Ile Ala Leu His Phe Thr Asn Pro Glu Arg Glu Gly Arg Tyr<br>195                     200                          205 | | 720 |
| gca ttc ttt gct caa aca tta gac gag cag aat gta gat tat gat gtc<br>Ala Phe Phe Ala Gln Thr Leu Asp Glu Gln Asn Val Asp Tyr Asp Val<br>210                     215                        220                    225 | | 768 |
| ttt gca agc tca tgg tac ccg aat tgg cac gga aca tta gag aat ctg<br>Phe Ala Ser Ser Trp Tyr Pro Asn Trp His Gly Thr Leu Glu Asn Leu<br>                   230                        235                    240 | | 816 |
| acg act att ttt aac gag ata gcg gag acc tac gat aaa aaa gta atg<br>Thr Thr Ile Phe Asn Glu Ile Ala Glu Thr Tyr Asp Lys Lys Val Met<br>              245                        250                        255 | | 864 |
| atg gca gaa gtc tcg tat tcg tat aca aat gaa gac cgg aat gga gat<br>Met Ala Glu Val Ser Tyr Ser Tyr Thr Asn Glu Asp Arg Asn Gly Asp<br>    260                          265                        270 | | 912 |
| ccg att ggt acg gag gaa gtt ccg ggt tat tca atc tcc gta caa ggt<br>Pro Ile Gly Thr Glu Glu Val Pro Gly Tyr Ser Ile Ser Val Gln Gly<br>275                     280                          285 | | 960 |
| caa gct cac gta att aga gat gca att gat gcg gtg gcg agt att ggg<br>Gln Ala His Val Ile Arg Asp Ala Ile Asp Ala Val Ala Ser Ile Gly<br>290                     295                        300                    305 | | 1008 |
| gat gcg agt att ggg gat gcg ggt ata ggt gtg ttt tac tgg gag cca<br>Asp Ala Ser Ile Gly Asp Ala Gly Ile Gly Val Phe Tyr Trp Glu Pro<br>                   310                        315                    320 | | 1056 |
| gct tgg att gat cca gct gga tat acg gag gac gag cta tac gat att<br>Ala Trp Ile Asp Pro Ala Gly Tyr Thr Glu Asp Glu Leu Tyr Asp Ile<br>              325                        330                    335 | | 1104 |
| agg gaa aca cat ggc tct ggt tgg gca tca agc tac gca gct acc tac<br>Arg Glu Thr His Gly Ser Gly Trp Ala Ser Ser Tyr Ala Ala Thr Tyr<br>    340                          345                        350 | | 1152 |
| gat cca gag gat gca ggc aaa tat tac ggt gga acg tca gct gat gac<br>Asp Pro Glu Asp Ala Gly Lys Tyr Tyr Gly Gly Thr Ser Ala Asp Asp<br>355                     360                          365 | | 1200 |

```
gaa gga ttg ttt gat tat cat ggc cat cca tta cca tca atc aat gtg   1248
Glu Gly Leu Phe Asp Tyr His Gly His Pro Leu Pro Ser Ile Asn Val
370                 375                 380                 385 ttc aaa gat gtc tac act gga gct gtg aca gaa tta aag gtt gat cga   1296
Phe Lys Asp Val Tyr Thr Gly Ala Val Thr Glu Leu Lys Val Asp Arg
                390                 395                 400 ata cat gat gtt cat ctc cag att agc ctt ggt caa aca gca aag tta   1344
Ile His Asp Val His Leu Gln Ile Ser Leu Gly Gln Thr Ala Lys Leu
            405                 410                 415 cct gaa acg gta aca gtc agc ttt aat gac cga agt act cag gag gta   1392
Pro Glu Thr Val Thr Val Ser Phe Asn Asp Arg Ser Thr Gln Glu Val
        420                 425                 430 cca gta agc tgg gac gag gaa gca ttc cag caa gct cta gaa agt gga   1440
Pro Val Ser Trp Asp Glu Glu Ala Phe Gln Gln Ala Leu Glu Ser Gly
    435                 440                 445 ctg gga tca tat gtg att aac gga aca gta gaa gat gga caa caa gta   1488
Leu Gly Ser Tyr Val Ile Asn Gly Thr Val Glu Asp Gly Gln Gln Val
450                 455                 460                 465 aaa gca cat ctc gaa atc act caa gaa aat gtt gtg aag aat cct agt   1536
Lys Ala His Leu Glu Ile Thr Gln Glu Asn Val Val Lys Asn Pro Ser
                470                 475                 480 ttt gaa gat agt gag aga gcg atg tgg gag atc caa aga att caa aaa   1584
Phe Glu Asp Ser Glu Arg Ala Met Trp Glu Ile Gln Arg Ile Gln Lys
            485                 490                 495 gct tct cga gag tac ttc                                           1602
Ala Ser Arg Glu Tyr Phe
        500

<210> SEQ ID NO 12
<211> LENGTH: 534
<212> TYPE: PRT
<213> ORGANISM: Bacillus sp. P203

<400> SEQUENCE: 12

Met Ile Gln Met Lys Arg Met Phe Gly Thr Cys Leu Ala Val Ala Val
        -30                 -25                 -20

Leu Gly Ile Pro Thr Ile Gly Gly Gln Ala Gly Val Ala Asn Ala Ala
-15                 -10                 -5                  -1  1

Ser Glu Pro Val Gln Ser Glu Leu Phe Val Glu Lys Val Glu Gly Leu
                5                   10                  15

Asp Glu Asp Phe Ile Arg Gly Val Asp Ile Ser Ser Val Ile Ala Met
            20                  25                  30

Glu Asn Ser Gly Thr Val Tyr Tyr Asn Glu Gly Glu Glu Gln Asp
        35                  40                  45

Val Phe Gln Thr Phe Lys Glu Ala Gly Ala Asn Tyr Val Arg Val Arg
50                  55                  60                  65

Val Trp Asn Asp Pro Tyr Asp Ala Glu Gly Asn Ser Tyr Gly Gly Gly
                70                  75                  80

Asn Asn Asp Leu Glu Thr Ala Ile Glu Ile Gly Lys Arg Ala Thr Glu
            85                  90                  95

Asn Gly Met Lys Leu Leu Val Asp Phe His Tyr Ser Asp Phe Trp Ala
        100                 105                 110

Asp Pro Gly Lys Gln Phe Pro Pro Lys Ala Trp Glu Asn Leu Ser Leu
    115                 120                 125

Glu Glu Lys Lys Ala Glu Leu Tyr Asp Phe Thr Lys Asp Ser Leu Glu
130                 135                 140                 145

Glu Met Leu Ala Glu Gly Ile His Ile Gly Met Val Gln Ile Gly Asn
                150                 155                 160
```

Glu Thr Thr Asn Gly Leu Ala Gly Glu Tyr Asp Trp Ser Asn Ile Thr
             165                 170                 175

Ser Leu Ile Asn Glu Gly Ser Lys Ala Val Arg Glu Val Asp Glu Asp
         180                 185                 190

Ile Leu Ile Ala Leu His Phe Thr Asn Pro Glu Arg Glu Gly Arg Tyr
     195                 200                 205

Ala Phe Phe Ala Gln Thr Leu Asp Glu Gln Asn Val Asp Tyr Asp Val
210                 215                 220                 225

Phe Ala Ser Ser Trp Tyr Pro Asn Trp His Gly Thr Leu Glu Asn Leu
                 230                 235                 240

Thr Thr Ile Phe Asn Glu Ile Ala Glu Thr Tyr Asp Lys Lys Val Met
             245                 250                 255

Met Ala Glu Val Ser Tyr Ser Tyr Thr Asn Glu Asp Arg Asn Gly Asp
         260                 265                 270

Pro Ile Gly Thr Glu Glu Val Pro Gly Tyr Ser Ile Ser Val Gln Gly
     275                 280                 285

Gln Ala His Val Ile Arg Asp Ala Ile Asp Ala Val Ala Ser Ile Gly
290                 295                 300                 305

Asp Ala Ser Ile Gly Asp Ala Gly Ile Gly Val Phe Tyr Trp Glu Pro
                 310                 315                 320

Ala Trp Ile Asp Pro Ala Gly Tyr Thr Glu Asp Glu Leu Tyr Asp Ile
             325                 330                 335

Arg Glu Thr His Gly Ser Gly Trp Ala Ser Ser Tyr Ala Ala Thr Tyr
         340                 345                 350

Asp Pro Glu Asp Ala Gly Lys Tyr Tyr Gly Thr Ser Ala Asp Asp
355                 360                 365

Glu Gly Leu Phe Asp Tyr His Gly His Pro Leu Pro Ser Ile Asn Val
370                 375                 380                 385

Phe Lys Asp Val Tyr Thr Gly Ala Val Thr Glu Leu Lys Val Asp Arg
                 390                 395                 400

Ile His Asp Val His Leu Gln Ile Ser Leu Gly Gln Thr Ala Lys Leu
             405                 410                 415

Pro Glu Thr Val Thr Val Ser Phe Asn Asp Arg Ser Thr Gln Glu Val
         420                 425                 430

Pro Val Ser Trp Asp Glu Glu Ala Phe Gln Gln Ala Leu Glu Ser Gly
     435                 440                 445

Leu Gly Ser Tyr Val Ile Asn Gly Thr Val Glu Asp Gly Gln Gln Val
450                 455                 460                 465

Lys Ala His Leu Glu Ile Thr Gln Glu Asn Val Val Lys Asn Pro Ser
                 470                 475                 480

Phe Glu Asp Ser Glu Arg Ala Met Trp Glu Ile Gln Arg Ile Gln Lys
             485                 490                 495

Ala Ser Arg Glu Tyr Phe
         500

<210> SEQ ID NO 13
<211> LENGTH: 20
<212> TYPE: DNA
<213> ORGANISM: Artificial
<220> FEATURE:
<223> OTHER INFORMATION: Primer
<220> FEATURE:
<221> NAME/KEY: Primer
<222> LOCATION: (1)..(20)
<223> OTHER INFORMATION: Primer A2up

<400> SEQUENCE: 13
agcgtttgcg gccgcgatcc                                              20

<210> SEQ ID NO 14
<211> LENGTH: 21
<212> TYPE: DNA
<213> ORGANISM: Artificial
<220> FEATURE:
<223> OTHER INFORMATION: Primer
<220> FEATURE:
<221> NAME/KEY: primer
<222> LOCATION: (1)..(21)
<223> OTHER INFORMATION: Primer B

<400> SEQUENCE: 14
ttattcggtc gaaaaggatc c                                            21

<210> SEQ ID NO 15
<211> LENGTH: 34
<212> TYPE: DNA
<213> ORGANISM: Artificial
<220> FEATURE:
<223> OTHER INFORMATION: Primer
<220> FEATURE:
<221> NAME/KEY: Primer
<222> LOCATION: (1)..(34)
<220> FEATURE:
<221> NAME/KEY: Primer
<222> LOCATION: (1)..(34)
<223> OTHER INFORMATION: SigA2NotU-P

<400> SEQUENCE: 15
tcgcgatccg ttttcgcatt tatcgtgaaa cgct                              34

<210> SEQ ID NO 16
<211> LENGTH: 33
<212> TYPE: DNA
<213> ORGANISM: artificial
<220> FEATURE:
<223> OTHER INFORMATION: Primer
<220> FEATURE:
<221> NAME/KEY: Primer
<222> LOCATION: (1)..(33)
<220> FEATURE:
<221> NAME/KEY: Primer
<222> LOCATION: (1)..(33)
<223> OTHER INFORMATION: SigA2NotD-P

<400> SEQUENCE: 16
ccgcaaacgc tggtgaaagt aaaagatgct gaa                               33

<210> SEQ ID NO 17
<211> LENGTH: 25
<212> TYPE: DNA
<213> ORGANISM: artificial
<220> FEATURE:
<223> OTHER INFORMATION: primer
<220> FEATURE:
<221> NAME/KEY: primer
<222> LOCATION: (1)..(25)
<220> FEATURE:
<221> NAME/KEY: primer
<222> LOCATION: (1)..(25)
<223> OTHER INFORMATION: BOCAfwd

<400> SEQUENCE: 17
tagtccgtac atatgagaaa aacaa                                        25

<210> SEQ ID NO 18
<211> LENGTH: 26
<212> TYPE: DNA
<213> ORGANISM: artificial

```
<220> FEATURE:
<223> OTHER INFORMATION: primer
<220> FEATURE:
<221> NAME/KEY: primer
<222> LOCATION: (1)..(26)
<220> FEATURE:
<221> NAME/KEY: primer
<222> LOCATION: (1)..(26)
<223> OTHER INFORMATION: BOCArev

<400> SEQUENCE: 18
ttcaaagctt atagtgaaat ccaact                                              26

<210> SEQ ID NO 19
<211> LENGTH: 23
<212> TYPE: DNA
<213> ORGANISM: artificial
<220> FEATURE:
<223> OTHER INFORMATION: primer
<220> FEATURE:
<221> NAME/KEY: primer
<222> LOCATION: (1)..(23)
<220> FEATURE:
<221> NAME/KEY: primer
<222> LOCATION: (1)..(23)
<223> OTHER INFORMATION: pQECAfwd

<400> SEQUENCE: 19
atccgcatgc tgagaaaaac aaa                                                 23

<210> SEQ ID NO 20
<211> LENGTH: 27
<212> TYPE: DNA
<213> ORGANISM: artificial
<220> FEATURE:
<223> OTHER INFORMATION: Primer
<220> FEATURE:
<221> NAME/KEY: Primer
<222> LOCATION: (1)..(27)
<220> FEATURE:
<221> NAME/KEY: Primer
<222> LOCATION: (1)..(27)
<223> OTHER INFORMATION: pQECArev

<400> SEQUENCE: 20
aattaagctt aatagtgaaa tccaact                                             27

<210> SEQ ID NO 21
<211> LENGTH: 19
<212> TYPE: DNA
<213> ORGANISM: artificial
<220> FEATURE:
<223> OTHER INFORMATION: Primer
<220> FEATURE:
<221> NAME/KEY: Primer
<222> LOCATION: (1)..(19)
<220> FEATURE:
<221> NAME/KEY: Primer
<222> LOCATION: (1)..(19)
<223> OTHER INFORMATION: CAmitSEQrev

<400> SEQUENCE: 21
cacttggtga atggaaatg                                                      19
```

POLYPEPTIDES OF STRAIN *BACILLUS* SP. P203

CROSS-REFERENCE TO RELATED APPLICATIONS

This application is a 35 U.S.C. 371 national application of PCT/DK2006/000447 filed Aug. 15, 2006 which claims priority or the benefit under 35 U.S.C. 119 of Danish application no. PA 2005 01156 filed Aug. 16, 2005 and U.S. provisional application No. 60/709,264 filed Aug. 18, 2005, the contents of which are fully incorporated herein by reference.

FIELD OF THE INVENTION

The present invention relates to functional polypeptides encoded by polynucleotides comprised in the genome of strains of a novel *Bacillus* species *Bacillus plankortiensis*. The reference strain of this species is *Bacillus* sp. P203 deposited under DSM 17419. The invention relates further to the polynucleotides and constructs of such polynucleotides encoding such polypeptides or facilitating their expression as well as to method for preparing the polypeptide. Still further the invention relates to compositions comprising the polypeptides and polynucleotides and to uses of the polypeptide. Still further the invention relates to a bacterium *Bacillus* sp. P203 as deposited under accession number DSM 17419.

BACKGROUND OF THE INVENTION

Alkaliphilic *Bacillus* strains are in focus of industrial biotechnology. Alkaliphilic strains and especially enzymes of those species have great potential in biotechnical applications where enzymatic activity (or even maximum activity) at high pH values is required for biotechnical processes (Horikoshi: Alkaliphiles: *Some Applications of Their Products for Biotechnology*; Microbiology and Molecular Biology Reviews, Vol. 63, No. 4, 1999). Examples for alkaliphilic *Bacillus* strains as source for novel catalysts are *B. clausii, B. pseudofirmus, B. clarkii, B. gibsonii*. In the pursuit of novel enzymes it is also known to screen for such new enzymes by subjecting potential candidates to specific enzyme assays. This approach is limited to the availability of enzyme assays and does not allow the identification of functional enzymes or polypeptides for which the activity is still unknown.

Further, whole genome sequencing is a known method to obtain the information on all genes from a given microorganism e.g. as described in Fleischmann et al.; *Whole genome sequences and assembly of Haemophilus influenzae Rd*; Nature 269: 496-512; (1995).

Most enzymes for industrial use are enzymes which are secreted to the medium by a microorganism. However, only a few percent of a microorganisms' genome encodes secreted proteins. For example only approx. 4% of the *Bacillus subtilis* genome or its closest relatives encode secreted proteins (Van Dijl et al.: *Protein transport pathways in Bacillus subtilis: a genome-based road map*; in "*Bacillus subtilis* and its closest relatives—*From genes to cells*; p. 337-355; A. L. Sonenshein (ed.); ASM Press 2002).

One disadvantage of genome sequencing is that the vast majority of the obtained sequences encode non secreted proteins.

An additional disadvantage of genomic sequencing particular to eukaryotes such as fungi is that the genome size is many times larger than a bacterial genome making gene discovery by this method more costly and time consuming.

The random sequencing of cDNAs (Expressed sequence tags or ESTs) is another approach that allows for discovery of secreted proteins. In general, EST approaches suffer two drawbacks with regard to secreted protein identification; 1) Depending on the induction conditions used for the cDNA library sequenced, very few, typically between 0.5%-15% or even 1 and 5% of the cDNAs encode secreted proteins. 2) The clones all come from a cDNA pool derived from mRNAs that are present in the organism in proportion to the induction level of each particular gene.

Also known is signal trapping which is a method to identify genes including nucleotides encoding a signal peptide using a translational fusion to an extra cellular reporter gene lacking its own signal (WO 01/77315).

SUMMARY OF THE INVENTION

The present inventors have found a strain of a novel *Bacillus* species *Bacillus plankortiensis*. The reference/type strain of this species is *Bacillus* sp. P203 deposited under DSM 17419. The strain grows at pH (7-11) and at low temperatures (4-30° C.). This strain is interesting because the phylogenetic distance between the public known strains and strain DSM17419 is significant and because the growth conditions are similar to conditions for several applications for industrial enzymes.

The genome of a microorganism contains thousands of different genes; some encoding polypeptides some coding for RNAs. Only a limited number of the genes in the genome of a microorganism encode functional polypeptides which are secreted by the microorganism to the surrounding medium serving an external purpose for the microorganism. Such polypeptides are interesting for industry from the point of view that such polypeptides may be produced in considerable amounts in continuous processes without destroying the cells producing the polypeptides.

It is an object of the present invention to identify and provide polypeptides secreted from strain *Bacillus* sp. P203 deposited under accession number DSM 17419 which have functional purpose for the strain *Bacillus* sp. P203 because such polypeptides may not only be used for industrial purposes but they may also be produced in industrially relevant processes and amounts.

In a first aspect the invention provides functional polypeptides encoded by polynucleotides comprised in the genome of strains of *Bacillus* species *Bacillus plankortiensis* deposited under accession number DSM 17419, and an isolated mature functional polypeptide which is at least 70% identical to and exhibits the same function of a corresponding secreted polypeptide obtainable from the bacterium strain *Bacillus* sp. P203.

In further aspects the invention provides a polynucleotide encoding the polypeptide of the invention; a nucleotide construct comprising the polynucleotide encoding the polypeptide, operably linked to one or more control sequences that direct the production of the polypeptide in a host cell; a recombinant expression vector comprising the nucleotide construct of the invention and to a recombinant host cell comprising the nucleotide construct of the invention.

In still further aspects the invention provides a method of preparing a polypeptide of the invention comprising:
(a) cultivating a strain comprising a nucleotide sequence encoding a polypeptide of the invention which strain is capable of expressing and secreting the polypeptide and
(b) recovering the polypeptide.

In a further aspect the invention provides a composition comprising a polypeptide of the invention and a method for preparing such a composition comprising admixing the polypeptide of the invention with an excipient.

In a further aspect the invention provides a composition comprising a polynucleotide of the invention and a method for preparing such a composition comprising admixing the polynucleotide of the invention with an excipient.

In further aspects the invention provides use of the polypeptide of the invention or a composition comprising said polypeptide in various applications.

In a final aspect the invention provides an electronic storage medium comprising information of the amino acid sequence of polypeptides of the invention or the nucleotide sequences of the polynucleotide of the invention.

Sequence Listing

The present application contains information in the form of a sequence listing, which is appended to the application and also submitted on a data carrier accompanying this application. The contents of the data carrier are fully incorporated herein by reference.

SEQ ID NO: 1 encodes serine protease comprised in SEQ ID NO: 2; SEQ ID NO: 3 encodes the carbonic anhydrase comprised in SEQ ID NO: 4; SEQ ID NO: 5 encodes the carbonic anhydrase comprised in SEQ ID NO:6; SEQ ID NO: 7 encodes xylanase comprised in SEQ ID NO: 8; SEQ ID NO: 9 encodes rhamnogalacturonan lyase comprised in SEQ ID NO: 10; SEQ ID NO: 11 encodes galactanase comprised in SEQ ID NO: 12.

DETAILED DESCRIPTION OF THE INVENTION

Definitions

Figure 1:
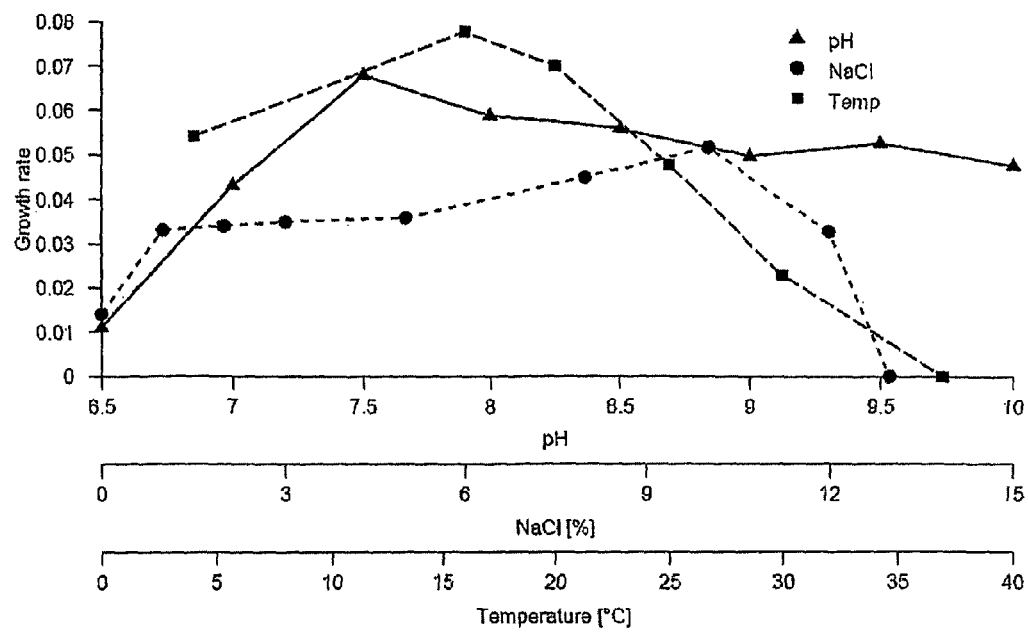
FIG. 1 shows growth characteristics of *Bacillus* sp. P203.

The term "identity" as used herein, is to be understood as the homology between two amino acid sequences or between two nucleotide sequences. For purposes of the present invention, the degree of identity between two amino acid sequences was determined by using AlignX in the program of Vector NTI ver. 7.1 (Informax inc., 7600. Wisconsin Avenue, Suite #1100, Bethesda, Md. 20814, USA). Amino acid alignment was created using the Clustal W algorithm (Nucleic Acid Research, 22 (22): 4673-4680, 1994). The following additional parameters are used: Gap opening penalty of 10, Gap extension penalty of 0.05, Gap separation penalty range of 8. Pairwise alignment parameters were Ktuple=1, gap penalty=3, gap length opening penalty=10, gap extension penalty=0.1, window size=5 and diagonals=5. The degree of identity between two nucleotide sequences is determined using the same algorithm and software package as described above for example with the following settings: Gap penalty of 10, and gap length penalty of 10. Pairwise alignment parameters is Ktuple=3, gap penalty=3 and windows=20.

The term "functional polypeptide" as used herein in the context of the present invention means a polypeptide which can be expressed and secreted by a cell and which constitutes an operational unit capable of operating in accordance with the function it is designed to fulfil by the cell. Optionally, co-factors may be required for the polypeptide to adopt the intended function. One example of functional polypeptides is catalytically active polypeptides or enzymes which help the cell catalyzing reactions in the environment surrounding the cell. Another example could be polypeptides which serve as signal substance. Further examples are polypeptides which function as sensors (receptors) for environmental parameters (chemicals in the environment surrounding the cell) or polypeptides, which are active against other organisms (antimicrobial (poly)peptides) or polypeptides, which contributes to the structural integrity of the cell.

The term "mature region" as used herein about portion of an amino acid sequences or polypeptide means the portion or region or domain or section of the amino acid sequences or polypeptide which is the mature functional polypeptide.

The term "region of nucleotide sequence encoding a mature polypeptide" as used herein means the region of a nucleotide sequence counting from the triplet encoding the first amino acid of a mature polypeptide to the last triplet encoding the last amino acid of a mature polypeptide.

The term "secreted polypeptide" as used herein is to be understood as a polypeptide which after expression in a cell is either transported to and released to the surrounding extra-cellular medium or is associated/embedded in the cellular membrane so that at least a part of the polypeptide is exposed to the surrounding extracellular medium.

Polypeptides of the Invention

The present invention relates to polypeptides similar to those secreted polypeptides obtainable from strain *Bacillus* sp. P203 deposited under accession number DSM 17419. In particular the invention provides an isolated mature functional polypeptide which is at least 70%, preferably 80% or more, such as 90%, 95%, 96%, 97%, 98% or 99% identical to and exhibits the same function of a corresponding secreted polypeptide obtainable from the strain *Bacillus* sp. P203 deposited under accession number DSM 17419.

Polypeptides of the invention are, in particular, secreted by strain *Bacillus* sp. P203 deposited under accession number DSM 17419 with the purpose of serving a function for that particular cell.

Among the thousands of potential genes in the genome of strain *Bacillus* sp. P203 deposited under accession number DSM 17419 the polynucleotides of this genome encoded 6 secreted functional mature polypeptides comprised in SEQ ID NO: 2, SEQ ID NO: 4, SEQ ID NO: 6, SEQ ID NO: 8, SEQ ID NO: 10 and SEQ ID NO: 12, which were determined to be functional, that is translated into functional polypeptides by the chosen host cell.

Further in a particular embodiment the genes encoding the said mature polypeptides can all be expressed and their corresponding mature polypeptides can be secreted when culturing an *E. coli* host transformed with polynucleotides comprising those regions of SEQ ID NO: 1, SEQ ID NO: 3, SEQ ID NO: 5, SEQ ID NO: 7, SEQ ID NO: 9 and SEQ ID NO: 11 encoding a mature polypeptide. By comparing homology or identity of the sequences of the 6 polypeptide sequences to known sequences the particular function of the polypeptides were annotated. All 6 secreted functional polypeptides were determined to be enzymes.

In particular the isolated polypeptide is selected from the group consisting of:
(a) a polypeptide having an amino acid sequence which has at least 70% identity with an amino acid sequence selected from the group consisting of the mature polypeptides comprised in SEQ ID NO: 2, SEQ ID NO: 4, SEQ ID NO: 6, SEQ ID NO: 8, SEQ ID NO: 10 and SEQ ID NO: 12, and (b) a polypeptide which is encoded by a nucleotide sequence which hybridize under high stringency conditions with a polynucleotide probe selected from the group consisting of
    (i) the complementary strand to a nucleotide sequence selected from the group consisting of regions of SEQ ID NO: 1, SEQ ID NO: 3, SEQ ID NO: 5, SEQ ID NO: 7, SEQ ID NO: 9 and SEQ ID NO: 11 encoding a mature polypeptide,
    (ii) the complementary strand to the cDNA sequence contained in a nucleotide sequences selected from regions of SEQ ID NO: 1, SEQ ID NO: 3, SEQ ID NO 5, SEQ ID NO: 7, SEQ ID NO: 9 and SEQ ID NO: 11 encoding a mature polypeptide;
wherein the polypeptide exhibits the function of the corresponding mature polypeptide of SEQ ID NO: 2, SEQ ID NO: 4, SEQ ID NO: 6, SEQ ID NO: 8, SEQ ID NO: 10 and SEQ ID NO: 12.

In one particular embodiment the polypeptide of the invention is selected among the enzymes secreted by strain *Bacillus* sp. P203 deposited under accession number 17419 and isolated by the present inventors, i.e. the group of enzymes consisting of xylanase, serine protease, carbonic anhydrase, rhamnogalacturonan lyase and galactanase.

The invention also provides an isolated enzyme selected from the group consisting of:
(a) an enzyme comprising an amino acid sequence which has at least 70% identity with the amino acid sequence of a mature enzyme selected from the group consisting of xylanase, serine protease, carbonic anhydrase, rhamnogalacturonan lyase and galactanase secreted from the strain of strain. *Bacillus* sp. P203 deposited under accession number 17419 and
(b) an enzyme which is encoded by a nucleotide sequence which hybridize under high stringency conditions with a polynucleotide probe selected from the group consisting of
    (i) the complementary strand to a nucleotide sequence comprised in the strain of strain *Bacillus* sp. P203 deposited under accession number 17419 encoding a mature enzyme selected from the group consisting of xylanase, serine protease, carbonic anhydrase, rhamnogalacturonan lyase and galactanase secreted from that strain;
    (ii) the complementary strand to the cDNA sequence contained in a nucleotide sequences comprised in the strain of strain *Bacillus* sp. P203 deposited under accession number DSM 17419 encoding a mature enzyme selected from the group consisting of xylanase, serine protease, carbonic anhydrase, rhamnogalacturonan lyase and galactanase secreted from that strain and
wherein the enzyme have a function selected from xylanase, serine protease, carbonic anhydrase, rhamnogalacturonan lyase and galactanase.

The polypeptide of the invention is an isolated polypeptide, preferably the preparation of the polypeptide of the invention contains at the most 90% by weight of other polypeptide material with which it may be natively associated (lower percentages of other polypeptide material are preferred, e.g. at the most 80% by weight, at the most 60% by weight, at the most 50% by weight, at the most 40% at the most 30% by weight, at the most 20% by weight, at the most 10% by weight, at the most 9% by weight, at the most 8% by weight, at the most 6% by weight, at the most 5% by weight, at the most 4% at the most 3% by weight, at the most 2% by weight, at the most 1% by weight and at the most 0.5% by weight). Thus, it is preferred that the isolated polypeptide of the invention is at least 92% pure, i.e. that the polypeptide of the invention constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. In particular, it is preferred that the polypeptide of the invention is in "essentially pure form, i.e. that the polypeptide preparation is essentially free of other polypeptide material with which it is natively associated. This can be accomplished, for example, by preparing the polypeptide of the invention by means of well-known recombinant methods.

The polypeptide of the invention of the invention may be synthetically made, naturally occurring or a combination thereof. In a particular embodiment the polypeptide of the invention may be obtained from a microorganism such as a prokaryotic cell, an archaeal cell or a eukaryotic cell. The cell may further have been modified by genetic engineering In a particular embodiment, the polypeptide of the invention is an enzyme exhibiting optimum enzyme activity at a temperature within the range from about 10° C. to about 80° C., particularly in the range from about 20° C. to about 60° C.

In a particular embodiment the polypeptide of the invention is an enzyme, which is functionally stabile at a temperature of up to 100° C., in particular up to 80° C., more particularly up to 60° C.

In a particular embodiment the polypeptide of the invention is an enzyme exhibiting at least 20%, in particular at least 40%, such as at least 50%, in particular at least 60%, such as at least 70%, more particularly at least 80%, such as at least 90%, most particularly at least 95%, such as about or at least 100% of the enzyme activity of an enzyme selected from mature enzymes comprised in SEQ ID NO: 2, SEQ ID NO: 4, SEQ ID NO: 6, SEQ ID NO: 8, SEQ ID NO: 10 and SEQ ID NO: 12.

In particular the isolated mature functional polypeptide is at least 70. % identical to and exhibits the same function of a corresponding secreted polypeptide obtainable from the bacterium strain *Bacillus* sp. P203 deposited under accession number DSM 17419 and specially the polypeptide of the invention comprises, contains or consists of an amino acid sequence which has at least 70% identity with a polypeptide sequence selected from the group consisting of mature polypeptides comprised in SEQ ID NO: 2, SEQ ID NO: 4, SEQ ID NO: 6, SEQ ID NO: 8, SEQ ID NO: 10 and SEQ ID NO: 12. The percent identity is particularly at least 95%, e.g. at least 96%, such as at least 97%, and even more particularly at least 98%, such as at least 99% or even 100% identity.

In another particular embodiment the percent identity is at least 50%; particularly at least 60%, particularly at least 65%, particularly at least 70%, particularly at least 75%, particularly at least 80%, and even more particularly at least 85% identity.

In a particular embodiment, the amino acid sequence of the polypeptide of the invention differs by at the most ten amino acids (e.g. by ten amino acids), in particular by at the most five amino acids (e.g. by five amino acids), such as by at the most four amino acids (e.g. by four amino acids), e.g. by at the most three amino acids (e.g. by three amino acids), in particular by at the most two amino acids (e.g. by two amino acids), such as by one amino acid from the mature polypeptides comprised in SEQ ID NO: 2, SEQ ID NO: 4, SEQ ID NO: 6, SEQ ID NO: 8, SEQ ID NO 10 and SEQ ID NO: 12.

The polypeptide of the invention may be a wild-type polypeptide isolated from a natural source such as the strain of strain *Bacillus* sp. P203, deposit number DSM 17419, or another wild type strain, however the present invention also encompass artificial variants, where a polypeptide of the invention has been mutated for example by adding, substituting and/or deleting one or more amino acids from said polypeptide while retaining the function of the polypeptide and/or other properties. Hence, the polypeptide of the invention may be an artificial variant, wherein at least one substitution, deletion and/or insertion of an amino acid has been made to an amino acid sequence comprising or consisting of the mature polypeptide comprised in SEQ ID NO: 2, SEQ ID NO: 4, SEQ ID NO: 6, SEQ ID NO: 8, SEQ ID NO: 10 and SEQ ID NO: 12.

The polypeptides of the invention also include functional fragments of the amino acid sequences described herein and nucleic acids encoding functional fragments of the amino acid sequences described herein, including fragments of the mature enzymes secreted from the strain, of strain *Bacillus* sp. P203, deposited under accession number DSM 17419, as described herein, including fragment of an enzyme selected from the group consisting of xylanase, serine protease, carbonic anhydrase, rhamnogalacturonan lyase and galactanase secreted from the strain of strain *Bacillus* sp. P203 deposited under accession number DSM 17419.

Artificial variants may be constructed by standard techniques known in the art usually followed by screening and/or characterization. Standard techniques includes classical mutagenesis, e.g. by UV irradiation of the cells or treatment of cells with chemical mutagens as described by Gerhardt et al. (1994); in vivo gene shuffling as described in WO 97/07205; in vitro shuffling as described by Stemmer, (1994) or WO 95/17413, random mutagenesis as described by Eisenstadt E. et al., (1994); PCR techniques as described by Poulsen et al. (1991); family shuffling as described by J. E. Ness, et al, Nature Biotechnology, vol. 17, pp. 893-896 (1999); site-directed mutagenesis as described by Sambrook et al. (1989), Sambrook et al., Molecular Cloning, A Laboratory Manual, Cold Spring Harbor, N.Y. A general description of nucleotide substitution can be found in e.g. Ford et al., 1991, Protein Expression and Purification 2, p. 95-107.

Such standard genetic engineering methods may also be used prepare a diversified library of variant nucleotide sequences from the genes encoding one or more parent enzymes of the invention, expressing the enzyme variants in a suitable host cell and selecting a preferred variant(s). A diversified library can be established by a range of techniques known to the art (Reetz M T; Jaeger K E, in Biocatalysis—from Discovery to Application edited by Fessner W D, Vol. 200, pp. 31-57 (1999); Stemmer, Nature, vol. 370, p. 389-391, 1994; Zhao and Arnold, Proc. Natl. Acad. Sci., USA, vol. 94, pp. 7997-8000, 1997; or Yano et al., Proc. Natl. Acad. Sci., USA, vol. 95, pp 5511-5515, 1998).

In a particular embodiment of the invention, amino acid changes (in the artificial variant as well as in wild-type enzyme) are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter and or impair the function of a protein are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a particular embodiment the amino acid changes are of such a nature that the physico-chemical properties of the polypeptides are altered. For example, amino acid changes may be performed, which improve the thermal stability of the enzyme, which alter the substrate specificity, which changes the pH optimum, and the like.

Particularly, the number of such substitutions, deletions and/or insertions in the polypeptide of the invention, particularly in those polypeptides selected from the group consisting of mature polypeptides comprised in SEQ ID NO: 2, SEQ ID NO: 4, SEQ. ID NO: 6, SEQ ID NO: 8, SEQ ID NO: 10 and SEQ ID NO: 12 to produce an artificial variant is at the most 10, such as at the most 9, e.g. at the most 8, more preferably at the most 7, e.g. at the most 6, such as at the most 5, most preferably at the most 4, e.g. at the most 3, such as at the most 2, in particular at the most 1.

In a particular embodiment the artificial variant is a variant, which has an altered, preferably reduced, immunogenicity, especially allergenicity, in animals including man as compared to a parent enzyme. The term "immunogenicity in this context is to be understood as the artificial variant capability of invoking a an altered, in particular reduced, immunological response when administered to an animal, including intravenous, cutaneous, subcutaneous, oral and intratracheal administration. The term "immunological response in this context means that the administration of the artificial variant causes an alteration in the immunoglobulin levels in the animal body, such as in IgE, IgG and IgM or an alteration in the cytokine level in the animal body. Methods for mapping immunogenic/antigenic epitopes of a protein, preparing variants with altered immunogenicity and methods for measuring an immunological response is well known to the art and are described e.g. in WO 92/10755, WO 00/26230, WO 00/26354 and WO 01/31989. The term "allergenicity in this context is to be understood as the artificial variant ability of invoking an altered, in particular reduced, production of IgE in an animal as well as the ability to bind IgE from said animal. Particularly allergenicity arising from intratracheal administration of the polypeptide variant to the animal is particularly of interest (also known as respiratory allergenicity).

In a further embodiment, the polypeptide of the invention is a polypeptide which is encoded by nucleotide sequences which hybridize under at least high stringency conditions, particularly under very high stringency conditions with a polynucleotide probe selected from the group consisting of
(i) the complementary strand to a nucleotide sequence selected from the group of regions of SEQ ID NO: 1, SEQ ID NO: 3, SEQ ID NO: 5, SEQ ID NO: 7, SEQ ID NO: 9 and SEQ ID NO: 11 encoding a mature polypeptide,
(ii) the complementary strand to the cDNA sequence contained in a nucleotide sequences selected from regions of SEQ ID NO: SEQ ID NO: 1, SEQ ID NO: 3, SEQ ID NO: 5, SEQ ID NO: 7, SEQ ID NO: 9 and SEQ ID NO: 11 encoding a mature polypeptide
(iii) a fragment of (i) or (ii) encoding a secreted polypeptide having the function of the corresponding mature polypeptide comprised in SEQ ID NO: 2, SEQ ID NO: 4, SEQ ID NO: 6, SEQ ID NO: 8, SEQ ID NO: 10 and SEQ ID NO: 12 (J. Sambrook, E. F. Fritsch, and T. Maniatus, 1989, Molecular Cloning, A Laboratory Manual, 2d edition, Cold Spring Harbor, N.Y.).

In particular, the polypeptide of the invention is encoded by a polynucleotide comprising a nucleotide sequence selected from the group of regions of SEQ ID NO: 1, SEQ ID NO: 3, SEQ ID NO: 5, SEQ ID NO: 7, SEQ ID NO: 9 and SEQ ID NO: 11 encoding a mature polypeptide or a sequences differing there from by virtue of the degeneracy of the genetic code. More particularly, the polypeptide of the invention is encoded by a polynucleotide consisting of a nucleotide sequence selected from the group of regions of SEQ ID NO: 1, SEQ ID NO: 3, SEQ ID NO: 5, SEQ ID NO: 7, SEQ ID NO: 9 and SEQ ID NO: 11 encoding a mature polypeptide or a sequence differing there from by virtue of the degeneracy of the genetic code.

The nucleotide sequences of regions of SEQ ID NO: 1, SEQ ID NO: 3, SEQ ID NO: 5, SEQ ID NO: 7, SEQ ID NO: 9 and SEQ ID NO: 11 encoding a mature polypeptide or a subsequence thereof, as well as the amino acid sequences of the mature polypeptides comprised in SEQ ID NO: 2, SEQ ID NO: 4, SEQ ID NO: 6, SEQ ID NO: 8, SEQ ID NO: 10 and SEQ ID NO: 12 or a fragment thereof, may be used to design a polynucleotide probe to identify and clone DNA encoding enzymes of the invention from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, more preferably at least 35 nucleotides in length, such as at least 70 nucleotides in length. It is; however, preferred that the polynucleotide probe is at least 100 nucleotides in length. For example, the polynucleotide probe may be at least 200 nucleotides in length, at least 300 nucleotides in length, at least 400 nucleotides in length or at least 500 nucleotides in length. Even longer probes may be used, e.g., polynucleotide probes which are at least 600 nucleotides in length, at least 700 nucleotides in length, at least 800 nucleotides in length, or at least 900 nucleotides in length. Both DNA and RNA probes can be used. The probes are typically labelled for detecting the corresponding gene (for example, with $^{32}$P, $^{3}$H, $^{35}$S, biotin, or avidin).

Thus, a genomic DNA or cDNA library prepared from such other organisms may be screened for DNA, which hybridizes with the probes described above and which encodes enzymes of the invention. Genomic or other DNA from such other organisms may be separated by agarose or polyacrylamide gel electrophoresis, or other separation techniques. DNA from the libraries or the separated DNA may be transferred to, and immobilized, on nitrocellulose or other suitable carrier materials. In order to identify a clone or DNA which has the required homology and/or identity or is homologous and/or identical with of nucleotides selected from regions of SEQ ID NO: 1, SEQ ID NO: 3, SEQ ID NO: 5, SEQ ID NO: 7, SEQ ID NO: 9 and SEQ ID NO: 11 encoding a mature polypeptide, the carrier material with the immobilized DNA is used in a Southern blot.

For purposes of the present invention, hybridization indicates that the nucleotide sequence hybridizes to a labelled polynucleotide probe which again hybridizes to a nucleotide sequence selected from regions of SEQ ID NO: 1, SEQ ID NO: 3, SEQ ID NO: 5, SEQ ID NO: 7, SEQ ID NO: 9 and SEQ ID NO: 11 encoding a mature polypeptide under high to very high stringency conditions. Molecules to which the polynucleotide probe hybridizes under these conditions may be detected using X-ray film or by any other method known in the art. Whenever the term "polynucleotide probe is used in the present context, it is to be understood that such a probe contains at least 15 nucleotides.

In an interesting embodiment, the polynucleotide probe is the complementary strand of a nucleotide sequence selected from regions of SEQ ID NO: 1, SEQ ID NO: 3, SEQ ID NO: 5, SEQ ID NO: 7, SEQ ID NO: 9 and SEQ ID NO: 11 encoding a mature polypeptide.

In another interesting embodiment, the polynucleotide probe is the complementary strand of a nucleotide sequence which encodes an enzyme selected from the group of SEQ ID NO: 1, SEQ ID NO: 3, SEQ ID NO: 5, SEQ ID NO: 7, SEQ ID NO: 9 and SEQ ID NO: 11. In a further interesting embodiment, the polynucleotide probe is the complementary strand of a mature polypeptide coding region of a nucleotide sequence selected from regions of SEQ ID NO: 1, SEQ ID NO: 3, SEQ ID NO: 5, SEQ ID NO: 7, SEQ ID NO: 9 and SEQ ID NO: 11 encoding a mature polypeptide.

For long probes of at least 100 nucleotides in length, high to very high stringency conditions are defined as pre-hybridization and hybridization at 42° C. in 5×SSPE, 1.0% SDS, 5×Denhardt's solution, 100 microgram/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 0.1×SSC, 0.1% SDS at 60° C. (high stringency), in particular washed three times each for 15 minutes using 0.1× SSC, 0.1% SDS at 68° C. (very high stringency).

Although not particularly preferred, it is contemplated that shorter probes, e.g. probes which are from about 15 to 99 nucleotides in length, such as from about 15 to about 70 nucleotides in length, may be also be used. For such short probes, stringency conditions are defined as pre-hybridization, hybridization, and washing post-hybridization at 5° C. to 10° C. below the calculated Tm using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated Tm.

SEQ ID NO: 2, Serine Protease

In a particular embodiment the polypeptide of the invention is an serine protease comprising or consisting of an amino acid sequence which has at least 70%, such as at least 80% or 85%, particularly at least 95%, more particularly at least 96%, more particularly at least 97%, more particularly at least 98%, more particularly at least 99% or most particularly 100% identity with an serine protease obtainable from strain *Bacillus* sp. P203, in particular that strain of strain *Bacillus* sp. P203 deposited under accession number DSM 17419, more particularly the mature serine protease comprised in SEQ ID NO: 2. The serine protease of the present invention is further described in Example 4.

SEQ ID NO: 4, Carbonic Anhydrase

In a particular embodiment the polypeptide of the invention is an carbonic anhydrase comprising or consisting of an amino acid sequence which has at least 70%, such as at least 80% or 85%, particularly at least 95%, more particularly at least 96%, more particularly at least 97%, more particularly at least 98%, more particularly at least 99% or most particularly 100% identity with a carbonic anhydrase obtainable from strain *Bacillus* sp. P203, in particular that strain of strain *Bacillus* sp. P203 deposited under accession number DSM 17419, more particularly the mature carbonic anhydrase comprised in SEQ ID NO: 4. The carbonic anhydrase of the present invention is further described in Example 8.

SEQ ID NO: 6, Carbonic Anhydrase

In a particular embodiment the polypeptide of the invention is an carbonic anhydrase comprising or consisting of an amino acid sequence which has at least 70%, such as at least 80% or 85%, particularly at least 95%, more particularly at least 96%, more particularly at least 97%, more particularly at least 98%, more particularly at least 99% or most particularly 100% identity with a carbonic anhydrase obtainable from strain *Bacillus* sp. P203, in particular that strain of strain *Bacillus* sp. P203 deposited under accession number DSM 17419, more particularly the mature carbonic anhydrase comprised in SEQ ID NO: 6.

SEQ ID NO: 8, Xylanase

In a particular embodiment the polypeptide of the invention is an xylanase comprising or consisting of an amino acid sequence which has at least 70%, such as at least 80% or 85%, particularly at least 95%, more particularly at least 96%, more particularly at least 97%, more particularly at least 98%, more particularly at least 99% or most particularly 100% identity with a xylanase obtainable from strain *Bacillus* sp. P203, in particular that strain of strain *Bacillus* sp. P203 deposited under accession number DSM 17419, more particularly the mature xylanase comprised in SEQ ID NO: 8. The xylanase of the present invention is further described in Example 6.

SEQ ID NO: 10, Rhamnogalacturonan Lyase

In a particular embodiment the polypeptide of the invention is a rhamnogalacturonan lyase comprising or consisting of an amino acid sequence which has at least 70%, such as at least 80% or 85%, particularly at least 95%, more particularly at least 96%, more particularly at least 97%, more particularly at least 98%, more particularly at least 99% or most particularly 100% identity with a rhamnogalacturonan lyase obtainable from strain *Bacillus* sp. P203, in particular that strain of strain *Bacillus* sp. P203 deposited under accession number DSM 17419, more particularly the mature rhamnogalacturonan lyase comprised in SEQ ID NO: 8. The rhamnogalacturonan lyase of the present invention is further described in Example 5.

SEQ ID NO: 12, Galactanase

In a particular embodiment the polypeptide of the invention is a galactanase comprising or consisting of an amino acid sequence which has at least 70%, such as at least 80% or 85%, particularly at least 95%, more particularly at least 96%, more particularly at least 97%, more particularly at least 98%, more particularly at least 99% or most particularly 100% identity with a galactanase obtainable from strain *Bacillus* sp. P203, in particular that strain of strain *Bacillus* sp. P203 deposited under accession number DSM 17419, more particularly the mature galactanase comprised in SEQ ID NO: 8. The galactanase of the present invention is further described in Example 7.

Polynucleotides

The present invention also relates to polynucleotides, particularly isolated polynucleotides, comprising or consisting of a nucleotide sequence encoding a polypeptide of the invention. In a particular embodiment, the nucleotide sequence is set forth in SEQ ID NO: 1, SEQ ID NO: 3, SEQ ID NO: 5, SEQ ID NO: 7, SEQ ID NO: 9 and SEQ ID NO: 11 including nucleotide sequences differing there from by virtue of the degeneracy of the genetic code. In a further embodiment the polynucleotide of the invention is a modified nucleotide sequence which comprises or consists of a nucleotide sequence selected from the regions of SEQ ID NO: 1, SEQ ID NO: 3, SEQ ID NO: 5, SEQ ID NO: 7, SEQ ID NO: 9 and SEQ ID NO: 11 encoding a mature polypeptide and which comprises at least one modification/mutation compared with the parent nucleotide sequence comprised in SEQ ID NO: 1, SEQ ID NO: 3, SEQ ID NO: 5, SEQ ID NO: 7, SEQ ID NO: 9 and SEQ ID NO: 11.

The techniques used to isolate and/or clone a nucleotide sequence encoding an enzyme are known in the art and include isolation from genomic DNA, preparation from cDNA, or a combination thereof. The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis et al, 1990, *PCR: A Guide to Methods and Application*, Academic Press, New York. Other amplification procedures such as ligase chain reaction (LCR), ligated activated transcription (LAT) and nucleotide sequence-based amplification (NASBA) may be used.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semi-synthetic, synthetic origin, or any combinations thereof.

In particular the polynucleotide comprises, preferably consists of, a nucleotide sequence which has at least 50% identity with a nucleotide sequence selected from the regions of SEQ ID NO: 1, SEQ ID NO: 3, SEQ ID NO: 5, SEQ ID NO: 7, SEQ ID NO: 9 and SEQ ID NO: 11 encoding a mature polypeptide. Particularly, the nucleotide sequence has at least 65% identity, more particularly at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with a nucleotide sequence selected from the regions of SEQ ID NO: 1, SEQ ID NO: 3, SEQ ID NO: 5, SEQ ID NO: 7, SEQ ID NO: 9 and SEQ ID NO: 11 encoding a mature polypeptide. Particularly, the nucleotide sequence comprises a nucleotide sequence selected from the regions of SEQ ID NO: 1, SEQ ID NO: 3, SEQ ID NO: 5, SEQ ID NO: 7, SEQ ID NO: 9 and SEQ ID NO: 11 encoding a mature polypeptide. In an even more particular embodiment, the nucleotide sequence consists of a nucleotide sequence selected from the regions of SEQ ID NO: 1, SEQ ID NO: 3, SEQ ID NO: 5, SEQ ID NO: 7, SEQ ID NO: 9 and SEQ ID NO: 11 encoding a mature polypeptide.

In particular the polynucleotide comprises, preferably consists of, a nucleotide sequence encoding a mature enzyme selected from xylanase, serine protease, carbonic anhydrase, rhamnogalacturonan lyase and galactanase and which has at least 50% identity, particularly at least 65% identity, more particularly at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with a nucleotide sequence encoding a mature enzyme selected from xylanase, serine protease, carbonic anhydrase, rhamnogalacturonan lyase and galactanase secreted from the strain of strain *Bacillus* sp. P203 deposited under accession number 17419.

SEQ ID NO: 1

In a particular embodiment the polynucleotide of the invention encodes a serine protease and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of SEQ ID NO: 1 encoding a mature serine protease.

SEQ ID NO: 3

In a particular embodiment the polynucleotide of the invention encodes a carbonic anhydrase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of SEQ ID NO: 3 encoding a mature carbonic anhydrase.

SEQ ID NO: 5

In a particular embodiment the polynucleotide of the invention encodes a carbonic anhydrase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of SEQ ID NO: 5 encoding a mature carbonic anhydrase.

SEQ ID NO: 7

In a particular embodiment the polynucleotide of the invention encodes a xylanase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of SEQ ID NO: 7 encoding a mature xylanase.

SEQ ID NO: 9

In a particular embodiment the polynucleotide of the invention encodes a rhamnogalacturonan lyase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of SEQ ID NO: 9 encoding a mature rhamnogalacturonan lyase,

SEQ ID NO: 11

In a particular embodiment the polynucleotide of the invention encodes a galactanase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of SEQ ID NO: 11 encoding a mature galactanase.

Modification of a nucleotide sequence encoding a polypeptide of the present invention may be necessary for the synthesis of a polypeptide which comprises an amino acid sequence that has at least one substitution, deletion and/or insertion as compared to an amino acid sequence selected from mature polypeptide comprised in SEQ ID NO: 2, SEQ ID NO: 4, SEQ ID. NO: 6, SEQ ID NO: 8, SEQ ID NO: 10 and SEQ ID NO: 12.

It will be apparent to those skilled in the art that such modifications can be made to preserve the function of the enzyme i.e. made outside regions critical to the function of the enzyme. Amino acid residues which are essential to the function are therefore preferably not subject to modification, such as substitution. Amino acid residues essential to the function may be identified according to procedures known in the art, such as site-directed mutagenesis or alanine-scanning mutagenesis (see, e.g., Cunningham and Wells, 1989, *Science* 244: 1081-1085). Sites of substrate-enzyme interaction can be determined by analysis of the three-dimensional structure as determined by such techniques as nuclear magnetic resonance analysis, crystallography or photoaffinity labeling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Moreover, a nucleotide sequence encoding an enzyme of the invention may be modified by introduction of nucleotide substitutions which do not give rise to another amino acid sequence of the enzyme encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a super coiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI, which is specific for methylated and hemimethylated DNA to digest the parental DNA template and to select for mutation-containing synthesized DNA. Other procedures known in the art may also be used. For a general description of nucleotide substitution, one may consult with e.g., Ford et al., 1991, *Protein Expression and Purification* 2: 95-107.

The present invention also relates to a polynucleotide comprising, preferably consisting of, a nucleotide sequence which encodes a polypeptide of the invention and which hybridizes under high stringency conditions, preferably under very high stringency conditions with a polynucleotide probe selected from the group consisting of:

(i) the complementary strand to a nucleotide sequence selected from the regions of SEQ ID NO: 1, SEQ ID NO: 3, SEQ ID NO: 5, SEQ ID NO: 7, SEQ ID NO: 9 and SEQ ID NO: 11 encoding a mature polypeptide, (ii) the complementary strand to the cDNA sequence contained in a nucleotide sequences selected from the regions of SEQ ID NO: 1, SEQ ID NO: 3, SEQ ID NO: 5, SEQ ID NO: 7, SEQ ID NO: 9 and SEQ ID NO: 11 encoding a mature polypeptide and, (iii) a fragment of (i) or (ii) encoding a secreted mature polypeptide having the function of the corresponding mature polypeptides comprised in SEQ ID NO: 2, SEQ ID NO: 4, SEQ ID NO: 6, SEQ ID NO: 8, SEQ ID NO: 10 and SEQ ID NO: 12

As will be understood, details and particulars concerning hybridization of the nucleotide sequences will be the same or analogous to the hybridization aspects discussed in the section titled "polypeptides of the invention herein.

The present invention also encompasses a storage medium suitable for use in an electronic, preferably digital, device comprising information of the amino acid sequence of polypeptides of the invention or the nucleotide sequences of the polynucleotide of the invention, in particular any of the polypeptide or polynucleotide sequences of the invention in an electronic or digital form, such as binary code or other digital code. The storage medium may suitably be a magnetic or optical disk and the electronic device a computing device and the information may in particular be stored on the storage medium in a digital form.

Recombinant Expression Vectors.

The present invention also relates to recombinant expression vectors comprising the nucleic acid construct of the invention. The various nucleotide and control sequences described above may be joined together to produce a recombinant expression vector, which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers that permit easy selection of transformed cells. A selectable marker is a gene the product of which provides for biocide or viral resistance, resistance to heavy metals, prototrophy to auxotrophs, and the like.

Examples of bacterial selectable markers are the dal genes from Bacillus subtilis or Bacillus licheniformis, or markers that confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6.

The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Recombinant Host Cells.

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, e.g., a prokaryote or a non-unicellular microorganism, e.g., a eukaryote.

Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell.

In a preferred embodiment, the host cell is a fungal cell. "Fungi as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). In a more preferred embodiment, the fungal host cell is a yeast cell. "Yeast as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, P. A., Passmore, S. M., and Davenport, R. R., eds, *Soc. App. Bacteriol. Symposium Series* No. 9, 1980).

In an even more preferred embodiment, the yeast host cell is a *Candida*, *Hansenula*, *Kluyveromyces*, *Pichia*, *Saccharomyces*, *Schizosaccharomyces*, or *Yarrowia* cell.

In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium*, *Aspergillus*, *Fusarium*, *Humicola*, *Mucor*, *Myceliophthora*, *Neurospora*, *Penicillium*, *Thielavia*, *Tolypocladium*, or *Trichoderma*.

In a most preferred embodiment, the filamentous fungal host cell is an *Aspergillus awamori*, *Aspergillus foetidus*, *Aspergillus japonicus*, *Aspergillus nidulans*, *Aspergillus niger* or *Aspergillus oryzae* cell. In another most preferred embodiment, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens*, *Humicola lanuginosa*, *Mucor miehei*, *Myceliophthora thermophila*, *Neurospora crassa*, *Penicillium purpurogenum*, *Thielavia terrestris*, *Trichoderma harzianum*, *Trichoderma Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

The Donor Strain

The invention also provides a strain *Bacillus* sp. P203, as deposited under accession number DSM 17419, and compositions comprising this microorganism.

The invention also provides strains of the genus *Bacillus* consisting of a novel species (*Bacillus plakortiensis*). The novel species comprise alkali- and halo-tolerant *Bacillus* strains which grow from pH 7-11 and from 0-12% NaCl concentration in the media at temperatures ranging from 4-30° C. Optimal conditions were from 4-20 C, at pH 7.5 and in 10% NaCl. Strains of the novel species can be further distinguished from related strains by the following parameters: The strains could utilize glycerol, glucose, D-fructose, D-mannose, D-mannitol, arbutin, aesculin, salicine, gelatine, citrate, glyceryl tributyrate, D-maltose, D-trehalose, skimmed milk, AZCL-casein, AZCL-arabinan and AZCL-galactan but not starch, Tween 20, AZCL-xyloglucan, AZCLpullulan, AZCL-arabinoxylan, AZCL-dextrain, AZCL-cellulose, AZCL-beta-glucan, AZCL-xylan, red amylose, red pullulan and red starch. Hydrolysis of ONPG was observed. Indol production (using Kováçs reagent) was negative, Voges Proskauer reaction (acetoin production) and test for catalase and oxidase activity was positive.

Strain P203 had 98% nucleotide identity from 16S rDNA sequence to type strain *Bacillus gibsonii* (deposit number DSM8722). Growth characteristics of strain P203 are shown in FIG. 1. *Bacillus plakortiensis* is more related to *Bacillus gibsonii* than to any other known *Bacillus* species, based on comparative 16S rDNA analysis. However, DNA homology between *Bacillus* plakortiensis, strain P203, and the closest known *Bacillus* species *B. gibsonii* type strain is (25.8-29.5%) DNA-DNA hybridization and G+C DNA content, determined by reverse phase HPLC at the DSMZ, Braunschweig, Germany. DNA was isolated using a French press (Thermo Spectronic™) and purified by chromatography on hydroxyapatite as described by (Cashion, et al., 1977). DNA-DNA hybridization was carried out as described by Ley, J. D., Cattoir, H. & Reynaerts, A. (1970): The quantitative measurement of DNA hybridization from renaturation rates. *Eur J Biochem* 12, 133-42, with the modifications described by Huss, V. A. R., Festl, H. & Schleifer, K. H. (1983): Studies on the spectrophotometric determination of DNA hybridization from renaturation rates. *Syst Appl Microbiol* 4, 184-192., using a model Cary 100 Bio. UV/VIS-spectrophotometer equipped with a Peltier-thermostated 6×6 multi cell changer and a temperature controller with in situ temperature probe (Varian).

Methods for Preparing Enzyme Polypeptides

The present invention also relates to methods for producing an enzyme of the invention comprising (a) cultivating a strain comprising a nucleotide sequence encoding an enzyme of the invention which strain is capable of expressing and secreting the enzyme and (b) recovering the enzyme. In a particular embodiment the strain is a wild type strain such as the strain *Bacillus sp. P203* DSM 17419, while in another embodiment the strain is a recombinant host cell as described, supra.

In these methods of the invention, the cells are cultivated in a nutrient medium suitable for production of the enzyme using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). As the enzyme is secreted into the nutrient medium, the enzyme can be recovered directly from the medium.

The resulting enzyme may be recovered by methods known in the art. For example, the enzyme may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

The methods of the invention also include the TAST method of WO 01/77315 A1 on a sample of the strain *Bacillus* sp. P203 deposited under accession number 17419, i.e. by fusing genes (e.g. from a gene library) from the genome of the strain *Bacillus* sp. P203 deposited under accession number DSM 17419 with a gene encoding a signalless reporter, such as a beta-lactamase, via a transposon tag, growing host cell clones comprising the genes of the strain *Bacillus* sp. P203 DSM 17419 fused with a gene encoding a signalless reporter, such as a beta-lactamase, via a transposon tag in a medium revealing the presence of the reporter, such as an ampicillin containing medium, detecting clones secreting the reporter and isolating gene and polypeptide of the strain *Bacillus* sp. P203 deposited under accession number DSM 17419 comprised in that clone.

When growing host cell clones comprising the genes of the strain *Bacillus* sp. P203 deposited under, accession number 17419 fused with a gene encoding a signalless reporter, such as a beta-lactamase, via a transposon tag in a medium revealing the presence of the reporter, such as an ampicillin containing medium, only those clones expressing and secreting the reporter (e.g. beta-lactamase) will be detected (e.g. survive). However the reporter will only be secreted if the gene to which the reporter gene is fused has an intact promotor and ribosome binding site (i.e. a gene which is expressed by the cell to produce a polypeptide in real life), which can be recognized in the host strain, and if the reporter is translated so that the synthesized polypeptide is transported across the cytoplasma membrane and folded correctly. Hence, when inserting the fused gene into a selected host cell, those clones, for which a reporter presence is detected (e.g. ampicillin resistance), will contain a gene from the strain *Bacillus* sp. P203 deposited under accession number DSM 17419, which encodes a functional secreted polypeptide.

Transgenic Plants

The present invention also relates to a transgenic plant, plant part, or plant cell that has been transformed with a nucleotide sequence encoding an enzyme of the invention so as to express and produce the enzyme. In one embodiment the plant could be used as host for production of enzyme in recoverable quantities. The enzyme may be recovered from the plant or plant part. Alternatively, the plant or plant part containing the recombinant enzyme may be used as such for improving the quality of a food or feed, e.g., improving nutritional value, palatability, and rheological properties, or to destroy an antinutritive factor. In particular the plant or plant parts expressing the enzyme may be used as an improved starting material for production of fuel-alcohols or bio-ethanol.

The transgenic plant can be dicotyledonous (a dicot) or monocotyledonous (a monocot). Examples of monocot plants are grasses, such as meadow grass (blue grass, *Poa*), forage grass such as *festuca, lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing an enzyme of the invention may be constructed in accordance with methods known in the art. Briefly, the plant or plant cell is constructed by incorporating one or more expression constructs encoding an enzyme of the invention into the plant host genome and propagating the resulting modified plant or plant cell into a transgenic plant or plant cell.

Conveniently, the expression construct is a nucleic acid construct which comprises a nucleotide sequence encoding an enzyme of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the enzyme is desired to be expressed. For instance, the expression of the gene encoding an enzyme of the invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, Cell 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito at al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad at al., 1998, *Journal of Plant Physiology* 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitre and Higgins, 1994, *Plant Molecular Biology* 26: 85-93), or the aldP gene promoter from rice (Kagaya at al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the enzyme of the invention in the plant. For instance, the promoter enhancer element may be an intron which is placed between the promoter and the nucleotide sequence encoding an enzyme of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well known in the art.

The present invention also relates to methods for producing an enzyme of the invention comprising (a) cultivating a transgenic plant or a plant cell comprising a nucleotide sequence encoding an enzyme of the invention under conditions conducive for production of the enzyme and (b) recovering the enzyme.

Compositions Comprising Polypeptides and Methods for their Preparation

The invention provide a composition comprising a polypeptide of the invention and preferably an excipient and a method for preparing such a composition comprising admixing the polypeptide of the invention with an excipient. In particular the composition comprises at least two different polypeptides of the invention, preferably at least 3, more preferable at least 4, more preferable at least 5, more preferable at least 6. Most the composition comprises all polypeptides secreted when fermenting a sample of strain *Bacillus* sp. P203 deposited under accession number DSM 17419 or a mutant thereof wherein one or more genes has been deleted or added.

In a particular embodiment the polypeptide of the invention is the major (polypeptide) component of the composition, e.g., a mono-component composition. The excipient in this context is to be understood as any auxilliary agent or compound used to formulate the composition and includes solvent, carriers, stabilizers and the like.

The composition may further comprise one or more additional enzymes, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The compositions may be prepared in accordance with methods known in the art and may be in the form of a liquid or a solid composition. For instance, the enzyme composition may be formulated using methods known to the art of formulating polypeptides and/or pharmaceutical products, e.g. into coated or uncoated granules or micro-granules. The polypeptide of the invention may thus be provided in the form of a granule, preferably a non-dusting granule, a liquid, in particular a stabilized liquid, a slurry or a protected polypeptide. For certain applications, immobilization of the polypeptide on a solid matrix may be preferred.

The polypeptide to be included in the composition may be stabilized in accordance with methods known in the art e.g. by stabilizing the polypeptide in the composition by adding and antioxidant or reducing agent to limit oxidation of the polypeptide or it may be stabilized by adding polymers such as PVP, PVA, PEG or other suitable polymers known to be beneficial to the stability of polypeptides in solid or liquid compositions In a further embodiment the composition of the invention is a detergent composition which, in addition to the polypeptide of the invention, comprises a surfactant and optionally compounds selected from the group consisting of builders such as zeolites, bleaching agents such as percarbonate, bleach enhancers such as TAED or NOBS, suds suppressors, fragrants, etc.

In a further embodiment the composition of the invention is a feed composition that in addition to the polypeptide of the invention comprises a cereal or grain product.

In a further embodiment the composition of the invention is a food composition such as a baker's flour composition, a brewed product, a fruit juice, an oil or lard product comprising the polypeptide of the invention.

In a further embodiment the composition of the invention is a pulping composition, which in addition to the polypeptide of the invention, comprises pulp.

Use of Polypeptides or Compositions Comprising them

In still further aspects the invention provides use of the polypeptides or polynucleotides of the invention or a composition comprising said polypeptides or polynucleotides in various applications, particularly (technical) processes such as processes performed in industry or household, herein under for commercial research purposes. Hence the invention encompasses a process comprising employing a polypeptide of the invention or a polynucleotide of the invention in a (technical) industrial, research or household process.

In one embodiment the polypeptide or the composition of the invention is used for cleaning a cellulosic fabric.

In another embodiment the polypeptide or the composition of the invention is used to prepare a food or feed additive.

In yet another embodiment the polypeptide or the composition of the invention is used for treatment of lignolitic materials and pulp.

In particular carbonic anhydrase may be used for carbon fixation from $CO_2$ emission streams, e.g. in membrane reactors for separating $CO_2$ from gas streams using carbonic anhydrase for applications in e.g. electrical generation flue gas stacks, greenhouse gases, but also in unconventional applications such as pilot cockpits and astronaut's space suits to keep breathing air free of toxic $CO_2$ levels.

In another embodiment carbonic anhydrases may be useful to promote water purification or mineralization from aqueous media by producing bicarbonate that can complex with ions dissolved in the aqueous media, especially divalent ions such as calcium, and aid in flocculation or precipitation of these ions from aqueous media. Such precipitation can in some applications be used to reduce water-hardness, and in other applications can have an added benefit of increasing the weight, volume, or opacity of certain products, such as in the paper-making process, or in remediation of soils and rocks.

Further carbonic anhydrase may also used as targets for the drug development such as carbonic anhydrase inhibitors (e.g. sulphonamide derivatives).

Detergent Disclosure

The polypeptide of the invention may be added to and thus become a component of a detergent composition:

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the polypeptide of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine, or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase®, Savinase®, Primase®, Duralase®, Esperase®, and Kannase® (Novozymes A/S), Maxatase®, Maxacal®, Maxapem®, Properase®, Purafect®, Purafect OxP®, FN2®, and FN3® (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™ and Lipex (Novozymes A/S).

Amylases: Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme®, and Carezyme® (Novozymes), Clazinase®, and Puradax HA® (Genencor International Inc.), and KAC-500(B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme® (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides).

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 that is hereby incorporated as reference.

Deposited Microorganisms

The following microorganism were deposited by the applicant according to the Budapest Treaty on the International Recognition of the deposits of Microorganisms for the Purpose of Patent Procedures at Deutsche Sammlung von Mikroorganismen and Zellkulturen GmbH, Mascheroder Weg 1b, D-38124 Braunschweig, Germany:

23 Jun. 2005; strain *Bacillus* sp. P203; DSM accession number DSM 17419.

EXAMPLES

Example 1

Identifying Functional Polypeptides Secreted by Strain *Bacillus* sp. P203, DSM 17419

A. Genomic Library Construction

Chromosomal DNA from strain *Bacillus* sp. P203 (DSM 17419) was prepared by using standard molecular biology techniques (Ausuble et al. 1995 "Current protocols in molecular biology Publ: John Wiley and sons). The prepared DNA was partially cleaved with Mbo I and separated in a sucrose gradient by ultracentrifugation. Fragments of 3 to 10 kilobases were extracted, precipitated and resuspended in a suitable buffer.

A genomic library was made by using the Stratagene ZAP Express™ predigested Vector kit and Stratagene ZAP Express™ predigested Gigapack® cloning kit (BamHI predigested) (Stratagene Inc., USA) following the instructions/recommendations from the vendor. The resulting lambdaZAP library comprised $1.25 \times 10^8$ pfu of which 40,000 were collected for mass excision. The resulting 10,000 *E. coli* colonies were pooled and plasmids were prepared by using the Qiagen Spin Mini prep kit (Qiagen, Germany). The eluate of approx. 1 ml containing the plasmid DNA was precipitated in a centrifuge with 1 volume part of Na-acetate pH 5 and 2 volume parts 96% ethanol at 20000 rpm at 4° C., washed with 70% (v/v) ethanol, dried at room temperature and resuspended in 200 microliter TE buffer. The DNA concentration of the plasmid pool DNA of the strain *Bacillus* sp. P203 genomic library was 0.7 microgram/microliter.

B. Transposon Construction and Preparation

The rationale behind the methology of Transposon Assisted Signal Trapping (TAST) as described in WO 01/77315 A1 is to fuse all genes within a selected genome with a gene encoding a signalless beta-lactamase via a transposon tag. Hence when growing host cell clones comprising the genes of a genome fused with a gene encoding a signalless beta-lactamase via a transposon tag in an ampicillin containing medium only those clones expressing and secreting a beta-lactamase will survive. However the beta-lactamase will only be secreted if the gene to which the beta-lactamase gene is fused has an intact promotor and ribosome binding site (i.e. a gene which is expressed by the cell to produce a polypeptide in real life), which can be recognized in the host strain, and if the beta-lactamase is translated so that the synthesized polypeptide is transported across the cytoplasma membrane and folded correctly. Hence, when inserting the fused gene into a selected host cell, those clones, which are ampicillin resistant contains a gene which encodes a functional secreted polypeptide.

Usually, when employing the TAST methodology it is even not necessary to express the entire gene. When tagging the genes with a transposon, expression of the N-terminal part of the genes as protein fusion shows that the genes contain intact transcription, translation and secretion sequences. Hence expression of the N-terminal part of the genes as protein fusion is usually regarded as sufficient for assuring expression and secretion of the entire gene.

Thus it can be concluded that the genes obtained by the TAST method actually do encode secreted functional polypeptides.

Construction of a SigA4 Transposon Containing the Beta-Lactamase Reporter Gene:

Following the instructions of WO 01/77315 A1, the construction of a transposon containing a signal-less beta-lactamase gene was carried out using standard molecular biology techniques. The signal-less beta-lactamase gene was initially PCR amplified from the vector pUC19 using a proofreading polymerase (Pfu Turbo, Stratagene, USA). The resulting PCR fragment contained the restriction sites NotI and EcoRI in order to aid cloning. The plasmid pEntranceposon(Cam') containing the Entranceposon and the antibiotic resistance markers CAT (encoding chloramphencol resistance in the transposon) was obtained from Finnzymes, OY (Espoo Finland). The plasmid was digested with the restriction enzymes NotI and EcoRI, gel purified and ligated with the signal-less beta-lactamase containing fragment. The ligation was transformed into electro-competent DH10B cells and the *E. coli* clone containing the recombinant plasmid with the signal-less beta-lactamase was identified by restriction analysis and named SigA2.

For transposon preparation, a smaller derivative of SigA2 was constructed, which lacked the b/a gene encoding beta-lactamase: Two oligonucleotide primers SigA2NotU-P 5'-TCG CGA TCC GTT TTC GCA TTT ATC GTG AAA CGC T-3' (SEQ ID NO: 15) and SigA2NotD-P 5'-CCG CAA ACG CTG GTG AAA GTA AAA GAT GCT GAA-3' (SEQ ID NO: 16), which bind to the start and stop of the bla gene of SigA2 directing outwards were used PCR amplify SigA2 without the bla gene. An amplificate of approx. 3.6 kb generated in the this PCR reaction was relegated and transformed in to a suitable *E. coli* strain. A plasmid of 3.6 kb was isolated from a transformant which was able to grow on LB chloramphenicol but not on LB ampicillin. This plasmid maintained both BglII sites and lacks the active bla gene and was called pSig4 (see the patent application PA 2004000010).

60 microliter of pSigA4 plasmid DNA preparation with a concentration of 0.3 microgram/microliter was digested with BglII and separated on an agarose gel. The SigA2 transposon DNA band of 2 kb was eluted and purified by using the "GFX™PCR, DNA and Gel Band Purification Kit" (Amersham Pharmacia Biotech Inc, USA) according to the instructions of the vender and eluted in 200 microliter EB buffer.

C. Transposon Tagging

The transposon prepared from pSigA4 carries a 5'-truncated bla-gene encoding a beta-lactamase from which the secretion signal has been removed. The beta-lactamase conveys ampicillin resistance on *E. coli* only when the protein is secreted to the periplasm, whereas cytoplasmic, expression of beta-lactamase does not confer ampicillin resistance. Without a signal sequence, the beta-lactamase enzyme will not be transported to the periplasm and therefore the clone will not grow on media containing ampicillin. The signal-less beta-lactamase gene was contained within the transposon in such a way that there was a continuous open reading frame between the transposon border and the beta-lactamase coding region. In this way the modified transposon, when it transposes into a gene encoding a protein that is secreted, could cause an in-frame fusion with the target gene. This resulted in a fusion gene product that is secreted to the periplasm of E. coli and conveys resistance to the ampicillin. If the transposon integrated even in-frame into a gene encoding a non-secreted protein, the respective host will not become ampicillin resistance.

For the in vitro transposon tagging of the strain Bacillus sp. P203 genomic library 250 nanogram of SigA2 transposon were mixed with 2.5 microgramm of the DNA concentration of the plasmid pool DNA of the strain Bacillus sp. P203 genomic library, 2.5 microliter of Finnzymes MuA Transposase (0.22 microgram/microliter) and 10 microliter of 5× buffer from Finnzymes OY, Espoo, Finland) in a total volume of 50 microliter and incubated at 30° C. for 3 h and followed by heat inactivation at 75° C. for 10 min. The DNA was precipitated by addition of 5 microliter 3M Na-acetate pH 5 and 110 microliter 96% ethanol, incubated at −20° C. for 20 h and centrifuged for 30 min at 20000 rpm. The pellet was washed with 70% ethanol, dried and resuspended in 10 microliter TE buffer.

D. Transformation and Selection

Electro-competent E. coli DH10B cells were transformed by electroporation in a Biorad Gene Pulse device (50 uF, 25 mAmp, 1.8 kV with 5 microliter of the transposon tagged plasmid pool, mixed with 1 ml SOC medium, pre-incubated for 1 h at 37° C. and plated on LB with 25 microliter/mililiter ampicillin, 50 microliter/mililiter kanamycin, 10 microliter/mililiter chloramphenicol and incubated for 2-3 days at 30° C. Out of the resistant transformants 1152 colonies were selected. Templates for DNA sequencing from the signal trapped library were prepared by rolling circle amplification using the Templyphi 500 kit (Amersham Biosciences) according to the manufacturer's instructions.

E. Plasmid Preparation and Sequencing

Approximately 500 transposon tagged plasmids were sequenced with the A2up primer AGCGTTTGCGGCCGC-GATCC (SEQ ID NO: 13) which read upstream into the into the transposon tagged gene, and, in a second reaction, with B primer TTATTCGGTCGAAAAGGATCC (SEQ ID NO: 14) which read downstream into the transposon tagged gene.

F. Sequence Assembly and Annotation

The obtained sequences were assembled into contigs by using the program PhredPhrap (Brent Ewing, LaDeana Hillier, Michael C. Wendl, and Phil Green, Base-calling of automated sequencer traces using phred I. Accuracy assessment (1998) Genome Research 8:175-185; Brent Ewing and Phil Green, Base-calling of automated sequencer traces using phred II. Error probabilities (1998) Genome Research 8:186-194). The obtained contigs were subsequently compared to sequences available in standard public DNA and protein sequences databases by using the program BLASTX 2.0a19MP-WashU [14 Jul. 1998] [Build linux-x86 18:51:44 30 Jul. 1998] (Gish, Warren (1994-1997). Unpublished; Gish, Warren and David J. States (1993). Identification of protein coding regions by database similarity search. Nat. Genet. 3:266-72).

The obtained sequences were functional genes which encoded intact and functional polypeptides, because they were obtained as ampicillin resistant clones as explained supra.

Example 2

Determining Function by Homology

The function of the polypeptides SEQ ID NO: 2, SEQ ID NO: 4, SEQ ID NO: 6, SEQ ID NO: 8, SEQ ID NO: 10 and SEQ ID NO: 12 were annotated by sequences comparison with genes or polypeptides of known function. The polypeptides of the invention were compared to a list of closest related sequences from public and in-house databases of contig's. The contigs were subsequently compared to sequences available in standard public DNA and protein sequences databases by using the program BLASTX 2.0a19MP-WashU [14 Jul. 1998]. A careful analysis of sequence alignments of SEQ ID NO: 2, SEQ ID NO: 4, SEQ ID NO: 6, SEQ ID NO: 8, SEQ ID NO: 10 and SEQ ID NO: 12 to their closest related sequences with known function from other databases made it possible to predict the function of these polypeptides on the basis of the degree of amino acid identity. Even when the overall amino acid identity was below 40%, which usually makes it difficult to make a good prediction, we were able to predict the function of SEQ ID NO: 2, SEQ ID NO: 4, SEQ ID NO: 6, SEQ ID NO: 8, SEQ ID NO: 10 and SEQ ID NO: 12 by carefully analysing and interpreting the amino acid residues in the catalytic sites or in important regions of the polypeptide sequences. If the amino acids of the catalytic site of a known sequences were also present in the polypeptide of the invention, combined with a sufficient overall amino acid identity, it was concluded that the polypeptide from Bacillus sp. P203 (DSM 17419) had the same function as the known sequence.

Example 3

Preparing Polypeptides of SEQ ID NO: 2, SEQ ID NO: 4, SEQ ID NO: 6, SEQ ID NO: 8, SEQ ID NO: 10 and SEQ ID NO: 12

To prepare the polypeptides of SEQ ID NO: 2, SEQ ID NO: 4, SEQ ID NO: 6, SEQ ID NO: 8, SEQ ID NO: 10 and SEQ ID NO: 12, the genes comprised in SEQ ID NO: 1, SEQ ID NO: 3, SEQ ID NO: 5, SEQ ID NO: 7, SEQ ID NO: 9 and SEQ ID NO: 11 encoding these polypeptides are expressed by fusing the DNA encoding the open reading frame to DNA a promoter, ribosome-binding site and terminator suitable for genes expression in an appropriate host strain, for example Escherichia coli, Bacillus subtilis, Bacillus licheniformis or Bacillus clausii or a derivative of strain Bacillus sp. P203. The promoter can either be an inducible promotor or a constitutive promoter. Any signal sequences can be exchanged with a suitable signal peptide of another bacterium. The expression construct can either be part of a plasmid or of a linear DNA. It can be integrated into the chromosome of the host strain by recombination or it can be present in the host cell on a plasmid. Then the transformed cells carrying the gene of interest are grown in a suitable medium in the desired volume. If an inducible promoter is used, the gene expression is started by adding the inducer. Otherwise a no inducer is needed and the cells will be grown until a suitable amount of protein from the gene of interest is produced. Then the culture is harvested and the proteins are recovered by standard methods.

Example 4

Protease

The culture fluid or a cell lysate of a host strain synthesising and secreting a serine protease in a suitable buffer may be assayed for that activity. A suitable volume of such a sample is spotted on agarose plates which contain the insoluble chromogenic substrate AZCL-casein (Megazyme™) and a suitable buffer at suitable pH. The plate is incubated for an appropriate time, e.g. one day, at an appropriate temperature, e.g. 55° C. The activity is visible as blue halos around the spots. As an alternative to AZCL-casein non-labelled casein can be used. On non-labelled casein spotted on agarose plates, clearing zones form in the presence of a serine protease.

Example 5

Rhamnogalacturonan Lyase

Rhamnogalacturonan is a major polysaccharide found in the hairy regions of pectin. Rhamnogalacturonan lyase (PL4 and PL11) and rhamnogalacturonase (GH28) are enzymes that can degrade the rhamnogalacturonan backbone of pectin but have no specificity towards homogalacturonan. A suitable volume of the culture fluid or a cell lysate of a host strain synthesising and secreting a rhamnogalacturonan lyase in a suitable buffer at an appropriate temperature, e.g. 30° C. is used for measuring the activity. A suitable volume of such a sample is spotted on agarose plates which contain the insoluble chromogenic substrate AZCL-rhamnogalacturonan I (Megazyme). The plate is incubated for an appropriate time, e.g. one day at an appropriate temperature, e.g. 30° C. The activity is visible as blue halos around the spots. As an alternative AZCL-galactan or AZCL-debranched arabinan or non-labelled potato pectic galactan or rhamnogalacturonan is added to agar plates or as substrate solution to the enzyme assay. Enzyme activity can be detected as blue halos around the spots clearing zones or by methods published by Mutter, M. et al., *Characterization of Recombinant Rhamnogalacturonan alpha-L-Rhamnopyranosyl-(1, 4)-alpha-D-Galactopyranosyluronide Lyase from Aspergillus aculeatus*, Plant Physiol. (1998) 117: 141-152 and by McKie, V. et al., *A new family of rhamnogalacturonan lyases contains an enzyme that binds to cellulose*, Biochem. J. (2001) 355, 167-177

Example 6

Xylanase

Xylanases are endo-acting enzymes that cleave beta-1,4-xylose polymers. For the measurement of endo-1,4-beta-D-xylanase in enzyme preparations the Xylanase Assay Kit (Megazyme) may be used. Alternatively, a suitable volume of the culture fluid or a cell lysate of a host strain synthesising and secreting a xylanase in a suitable buffer at an appropriate temperature, e.g. 30° C. is used for measuring the activity. A suitable volume of such a sample is spotted on agarose plates which contain the insoluble chromogenic substrate AZCL-xylan or AZCL-arabinoxylan (Megazyme). The plate is incubated for an appropriate time, e.g. one day at an appropriate temperature, e.g. 30° C. The activity is visible as blue halos around the spots.

Example 7

Galactanase

Proteins of this type are hemicellulases that can hydrolyze short xylo-oligosaccharides, e.g. arabinan. The culture fluid or a cell lysate of a host strain synthesizing or secreting a galactanase in a suitable buffer may be assayed for that activity. A suitable volume of the culture fluid or a cell lysate of a host strain synthesizing and secreting a galactanase in a suitable buffer at an appropriate temperature, e.g. 30° C. is used for measuring the activity. A suitable volume of such a sample is spotted on agarose plates which contain the insoluble chromogenic substrate AZCL-arabinan (Megazyme). The plate is incubated for an appropriate time, e.g. one day at an appropriate temperature, e.g. 30° C. The activity is visible as blue halos around the spots.

Example 8

Expression of Carbonic Anhydrase from Strain Bacillus sp. P203 in B. Subtilis

The signal peptide from the alpha-amylase from *B. licheniformis* (AmyL) was fused by PCR in frame to the gene encoding the carbonic anhydrase (SEQ ID NO: 3). The DNA coding for the resulting coding sequence was integrated by homologous recombination on the *Bacillus subtilis* host cell genome. The gene construct was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyl-transferase was used as maker. (Described e.g in Diderichsen et al., *A useful cloning vector for Bacillus subtilis*. Plasmid, 30, p. 312, 1993).

Chloramphenicol resistant transformants were analyzed by DNA-sequencing to verify the correct DNA sequence of the construct. One such clone was selected.

Fermentations of the carbonic anhydrase (SEQ ID NO: 4) expression clone was performed on a rotary shaking table in 1 L baffled Erlenmeyer flasks each containing 400 ml LB media supplemented with 34 mg/l chloramphenicol. The clone was fermented for 3 days at 25-30° C. The carbonic anhydrase activity was determined according to Wilbur, K. M. and Anderson, N. G., *Electrometric and colorimetric determination of carbonic anhydrase*, J Biol Chem, 1948, 176, p. 147-154. Alternatively, the carbonic anhydrase activity can be measured as esterase activity with para-nitrophenolacetate as substrate according to Chirica, L. C. et al., *Cloning, expression and some properties of alpha-carbonic anhydrase from Helicobacter pylori*, Biochim. Biophys. Acta, 2001, 1544, p. 55-63. A standard assay contained 900 microliter of PNPA, 10 microliter of 300 mM Tris pH 7.5 and 90 microliter of carbonic anhydrase protein solution. After a pre-incubation for 5 min, the enzyme was added to the PNPA buffer mixture and the increase in absorbance (due to the hydrolysis of the substrate and release of p-nitrophenol) at 348 nm was monitored photometrically in a quartz cuvette over a period of 10 min. As a positive control for both activity assays, a solution of bovine carbonic anhydrase (Calbiochem, 1 mg per mL) may be used.

Example 9

Expression of Carbonic Anhydrase from Strain Bacillus sp. P203 in E. coli

Alternatively to example 8, the carbonic anhydrase can be expressed in *E. coli*. Plasmid pEG131377-9 was generated by ligation of the pGEM-T vector (Promega) with the carbonic anhydrase PCR product (SEQ NO. 3) amplified from *Bacillus* sp. P203 genomic DNA (extracted with Qiagen Genomic DNA Kit, 19060) using gene specific primers BOCAfwd (5' TAGTCCGTACATATGAGAAAAACAA 3') (SEQ ID NO:

17) and BOCArev (5' TTCAAAGCTTATAGTGAAATC-CAACT 3') (SEQ ID NO: 18). The plasmid was used as template for generation of plasmid pETBlueCA. The plasmid pETBlueCA for expression of the carbonic anhydrase in *E. coli* was constructed by PCR amplification with the gene specific primers pQECAfwd (5' ATCCGCATGCT-GAGAAAAACAAA 3') (SEQ ID NO: 19) and pQECArev (5' AATTAAGCTTAATAGTGAAATCCAACT 3') (SEQ ID NO: 20) from plasmid template pEG131377-9 followed by a ligation of the PCR product with the linear pETBlue-1 Accep-Tor™ vector system (Novagen) according to the manufacturer's instructions. Plasmids were trans-formed into chemical competent *E. coli* NovaBlue Singles™ cells (Novagen) for blue-white screening. Inserts of three plasmids were verified by DNA sequencing using primers pETBlueUP, pETBlue-DOWN (Novagen, primers flanking the insert region) and primer CAmitSEQrev (5' CACTTGGTGAATGGAAATG 3') (SEQ ID NO: 21). The plasmid pETBlueCA clone no. 8 (pETBlueCAB) was found correct and was transformed into chemical competent *E. coli* Tuner(DE3)pLacI cells for over-expression of carbonic anhydrase from *Bacillus* sp. P203 under control of the lac promoter (IPTG inducible).

Example 10

Purification and Characterization of Carbonic Anhydrase (SEQ ID NO: 4) from strain *Bacillus* sp. P203

Purification

Culture broth was centrifuged (10000 g, 15 minutes) and the supernatants were carefully decanted from the precipitates. The pooled culture supernatant was concentrated to $\frac{1}{10}$ of the volume by crossflow filtration (MW cutoff 10,000 Da) and purified on a carbonic anhydrase specific chromatography column. For purification of recombinant carbonic anhydrase from *Bacillus plankortiensis*, a highly selective affinity column was prepared. In principle, the affinity column was prepared as described before (Khalifah, R. G. et al., *Carbon-13 nuclear magnetic resonance probe of active-site ionizations in human carbonic anhydrase B*, Biochem. 1977, 16, p. 2241-7) with the following modifications: The sulfonamide ligand 4-aminomethylbenzenesulfonamide (0.2 g, Sigma) was dissolved in 12 mL of coupling buffer (0.1 M $NaHCO_3$, pH 8, 0.5 M NaCl). 1 g of activated CH Sepharose 4B™ (Amersham Biosciences) was dissolved in approx. 20 ml 1 mM HCl and thoroughly washed with 250 mL 1 mM HCl on a sintered glass filter. The gel was eluted from the filter with 6 mL of 1 mM HCl and given to the dissolved ligand in a 50 mL Falcon tube. The mixture was gently rotated end-over-end for 1 h at room temperature. To remove excess ligand, the gel was washed with 250 mL coupling buffer. Blocking of any remaining active groups was performed by washing the gel with 0.1 M Tris-HCl, pH 8 and incubating in that buffer for 1 hour. Three cycles of a) 250 mL 0.1 M Tris, pH 8, 0.5 M NaCl and b) 0.1 M sodium acetate, pH 4, 0.5 M NaCl were used to wash the gel after blocking. The gel was transferred in a beaker and washed extensively with loading buffer D (0.25 M $Na_2SO_4$, 25 mM Tris pH 8.3) prior to use.

5 mL of the affinity media was given to either 50 mL concentrated culture broth of example no. 8 or to the cell free raw protein extract of example no. 9. The suspension was smoothly agitated at room temperature for one hour and then poured into a column letting gravity packing the column. The column was washed intensively with 10 volumes of loading volume with buffer D until no protein further was detectable. Elution of carbonic anhydrase was started by closing the outlet and addition of 10 ml elution buffer E (0.4 M KSCN, 25 mM Tris pH 8.3). After 10 min of incubation with moderately shaking of the column, 500 microliter fractions were collected. Fractions containing carbonic anhydrase activity were pooled after the first active fraction (usually fractions 4-10). Pooled fractions were re-buffered intensively in a Centricon device (Millipore, at 4000×g) with a MW 10,000 Da cutoff using 10 volumes of carbonic anhydrase storage buffer F (100 mM Tris-HCl pH 8.0, 50 micromolar zinc sulphate). Aliquots of purified carbonic anhydrase were stored at −20° C. until further use. The purified recombinant carbonic anhydrase showed a single protein band on SDS polyacrylamid gels.

Characterization

Figure 2:
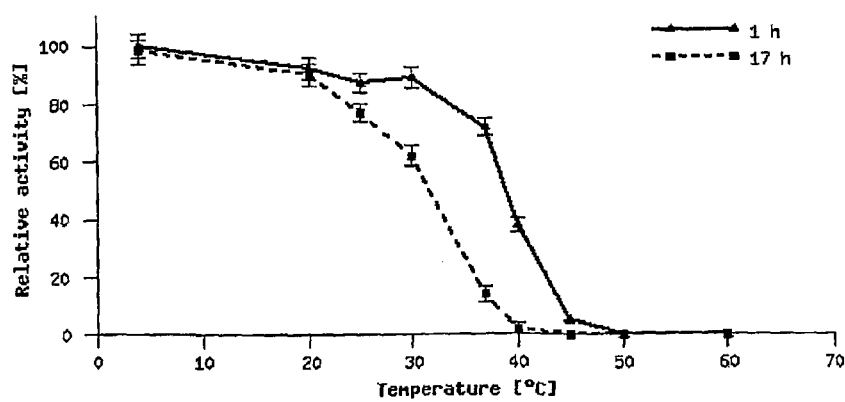
FIG. 2 shows stability of carbonic anhydrase from *Bacillus* sp. P203.

The carbonic anhydrase activity was determined according to Wilbur. K. M. and Anderson, N. G., *Electrometric and colorimetric determination of carbonic anhydrase*, J Biol Chem, 1948, 176, p. 147-154. The purified recombinant carbonic anhydrase was tested for temperature stability at 4-60° C. for 1 and 17 h. The protein was found to be stable at 4° C. in buffer F for a week with minimal loss of activity (97+/−4% of original activity) and at room temperature (20° C., 95+/−4% of original activity). No loss of activity (99+/−4% of original activity) was detected after storage of the protein at −20° C. for one week in buffer F. The stability of carbonic anhydrase rapidly decreased at temperatures over 37° C. (see FIG. 2). Storage of recombinant carbonic anhydrase in buffer F supplemented with 1 mM dithiothreitol (DTT) was found to stabilize the enzyme.

Figure 3:
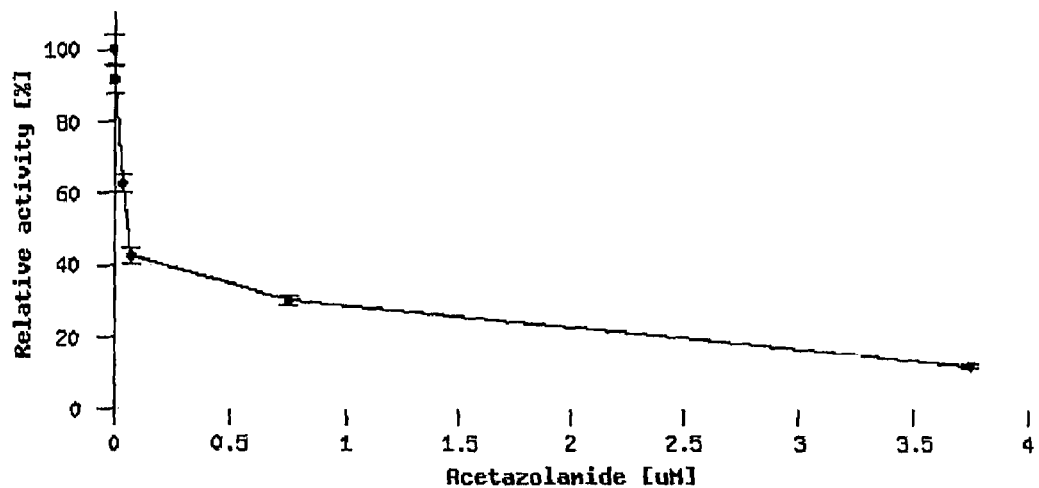
FIG. 3 shows inhibition of carbonic anhydrase with acetazolamide.

Inhibition studies of recombinant carbonic anhydrase were performed with azide ions and specific carbonic anhydrase inhibitor acetazolamide (Sigma). The $IC_{50}$ values were 500 micromolar for azide and 0.09 micromolar for acetazolamide, complete inhibition was observed in the presence of 7.5 micromolar acetazolamide (see FIG. 3).

Figure 4:
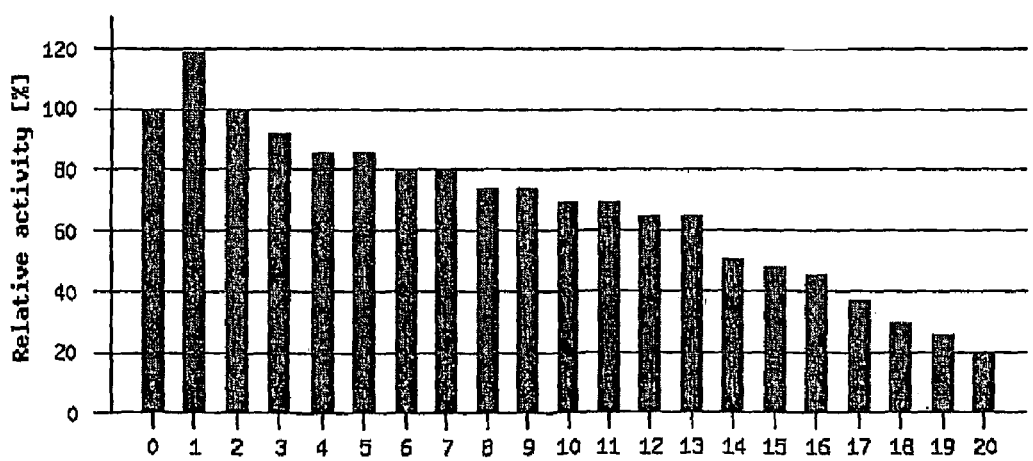
FIG. 4 shows inhibition of carbonic anhydrase with metal ions, azide and other reagents.

Inhibition of carbonic anhydrase by two and three valent metal ions, azide and other reagents commonly used in protein science (see FIG. 4):

The following inhibitors were used:

TABLE 1

| | Inhibitors |
|---|---|
| 0: | Control |
| 1: | $CaCl_2$ |
| 2: | $MnCl_2$ |
| 3: | EDTA |
| 4: | $NaWO_4$ |
| 5*: | $CrCl_3$ |
| 6: | Guanidin-HCl |
| 7: | beta-mercaptoethanol |
| 8: | SDS |
| 9*: | $FeCl_3$ |
| 10: | Urea |
| 11: | $MgCl_2$ |
| 12: | DTT |
| 13: | $Na_2SeO_3$ |
| 14: | $ZnSO_4$ |
| 15: | $(NH_4)Fe(SO_4)_2$ |
| 16: | $CoCl_2$ |
| 17*: | Triton X 100 |
| 18: | $CuSO_4$ |
| 19: | $NiSO_4$ |
| 20: | $NaN_3$ |

Enzyme was pre-incubated with 1 mM of the substances for 1 h on ice in a total volume of 50 micro liter before testing activity with 10 micro liter of the mixture with the Wilbur and Anderson, 1948 method. The control with no additives (water) was set to 100% activity. The detergent Triton X 100 and ions $Fe_{3+}$ and $Cr_{2+}$ (marked with asterixes in table 1) altered the assay when in given concentration of 1 mM in the total assay volume. Instead activity with 25 micro molar concentration of the chemicals are given.

Example 11

Expression of Galactanase

The signal peptide from the alpha-amylase from *B. licheniformis* (AmyL) was fused by PCR in frame to the gene encoding the galactanase (SEQ ID NO: 12). The DNA coding for the resulting coding sequence was integrated by homologous recombination on the *Bacillus subtilis* host cell genome. The gene construct was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyl-transferase was used as maker. (Described e.g in Diderichsen et al., *A useful cloning vector for Bacillus subtilis*. Plasmid, 30, p. 312, 1993).

Chloramphenicol resistant transformants were analyzed by DNA sequencing to verify the correct DNA sequence of the construct. One such clone was selected. Fermentations of the galactanase (SEQ ID NO: 12) expression clone was performed on a rotary shaking table in 500 ml baffled Erlenmeyer flasks each containing 100 ml LB media supplemented with 34 mg/l chloramphenicol. The clone was fermented for 3 days at 30° C. The activity was determined with OPNG as substrate.

Example 12

Verification of Galactanase Activity from Strain *Bacillus* sp. P203

Assay:

50 microliters of the cell free supernatant from example no. 7 were given to 750 microliters of a 4.5 mM solution of ortho-nitrohenylgalactopyranoside (ONPG), in 50 mM phosphate buffer pH 7.6. The mixture was incubated at 40° C. for 15 min and the reaction was stopped by addition of 300 microliters 1 M sodium carbonate. The solutions were centrifuged for 1 min at 13,000 rpm prior to spectrometric measurements and diluted with water if necessary. The absorbation of o-nitrophenolate is measured optically at 420 nm.

The invention claimed is:

1. An isolated polypeptide having carbonic anhydrase activity, selected from the group consisting of:

(a) a polypeptide comprising an amino acid sequence which has at least 90% sequence identity to SEQ ID NO: 4;

(b) a fragment of SEQ ID NO: 4 having carbonic anhydrase activity.

2. The polypeptide of claim 1, having at least 95% sequence identity to SEQ ID NO: 4.

3. The polypeptide of claim 1, having at least 96% sequence identity to SEQ ID NO: 4.

4. The polypeptide of claim 1, having at least 97% sequence identity to SEQ ID NO: 4.

5. The polypeptide of claim 1, having at least 98% sequence identity to SEQ ID NO: 4.

6. The polypeptide of claim 1, having at least 99% sequence identity to SEQ ID NO: 4.

7. The polypeptide of claim 1, which comprises SEQ ID NO: 4.

8. The polypeptide of claim 1, which consists of SEQ ID NO: 4.

9. A composition comprising the polypeptide of claim 1.

10. The composition of claim 9, further comprising one or more additional enzymes.

11. The composition of claim 9, further comprising a cereal or grain product.

12. The composition of claim 9, further comprising a polysaccharide or a mixture of polysaccharides.

13. A detergent composition comprising a polypeptide of claim 1 and a surfactant.

* * * * *